(12) United States Patent
Kurisawa et al.

(10) Patent No.: US 8,753,687 B2
(45) Date of Patent: Jun. 17, 2014

(54) PARTICULATE HYALURONIC ACID/FLAVONOID SUSPENSIONS FOR CELLULAR DELIVERY OF BIOACTIVE AGENTS

(75) Inventors: Motoichi Kurisawa, Singapore (SG); Shengyong Ng, Singapore (SG); Joo Eun Chung, Singapore (SG)

(73) Assignee: Agency for Science, Technology and Research, Singapore (SG)

( * ) Notice: Subject to any disclaimer, the term of this patent is extended or adjusted under 35 U.S.C. 154(b) by 0 days.

(21) Appl. No.: 13/390,097

(22) PCT Filed: Aug. 11, 2010

(86) PCT No.: PCT/SG2010/000297
§ 371 (c)(1),
(2), (4) Date: Feb. 10, 2012

(87) PCT Pub. No.: WO2011/019323
PCT Pub. Date: Feb. 17, 2011

(65) Prior Publication Data
US 2012/0148567 A1    Jun. 14, 2012

(30) Foreign Application Priority Data

Aug. 11, 2009  (SG) ............................. 200905341-4

(51) Int. Cl.
*A61K 9/50* (2006.01)
(52) U.S. Cl.
USPC ........................................................ 424/499
(58) Field of Classification Search
None
See application file for complete search history.

(56) References Cited

U.S. PATENT DOCUMENTS 7,858,080 B2 * 12/2010 Chung et al. ................. 424/78.3
2008/0102052 A1 * 5/2008 Chung et al. ................. 424/78.3

FOREIGN PATENT DOCUMENTS

WO    WO 2006/124000 A1    11/2006
WO    WO 2009/054813 A1    4/2009

OTHER PUBLICATIONS

"Nanoscale", wikipedia, Mar. 2013.*
PCT International Search Report for PCT Counterpart Application No. PCT/SG2010/000297, 3 pages, (Nov. 15, 2010).
PCT Written Opinion of the International Searching Authority for PCT Counterpart Application No. PCT/SG2010/000297, 5 pages, (Nov. 15, 2010).
Response to the Written Opinion mailed Nov. 15, 2010 for PCT Counterpart Application No. PCT/SG2010/000297, 6 pages, (May 27, 2011).
PCT International Preliminary Report on Patentability (Chapter II of the Patent Cooperation Treaty) for PCT Counterpart Application No. PCT/SG2010/000297, 4 pages, (Sep. 26, 2011).

(Continued)

*Primary Examiner* — Carlos Azpuru
(74) *Attorney, Agent, or Firm* — Blakely, Sokoloff, Taylor & Zafman LLP

(57) ABSTRACT

There is presently provided a suspension of immiscible particles in a solution, wherein the particles comprise an agglomeration of a bioactive agent, for example an anti-cancer agent; and a plurality of conjugates of a hyaluronic acid and a flavonoid, for example a catechin-based flavonoid, wherein the particles are on average from about 15 nm to about 300 nm in diameter and wherein the bioactive agent is releasably retained in the particles by the flavonoid. The suspension is useful for the delivery of the bioactive agent to cells, including cancer cells. There are also provided a therapeutic formulation comprising the suspension, as well as methods for using the suspension and therapeutic formulation, including for delivery of a bioactive agent to a cell and for treating a disease, including cancer.

11 Claims, 11 Drawing Sheets

(56) References Cited

OTHER PUBLICATIONS

J.W. Park, et al., "Tumor targeting using anti-her2 immunoliposomes", Journal of Controlled Release, vol. 74, Issues 1-3, pp. 95-113, (Jul. 6, 2011).
Peter D. Senter, et al., "Selective activation of anticancer prodrugs by monoclonal antibody-enzyme conjugates", Advanced Drug Delivery Reviews, vol. 53, Issue 3, pp. 247-264, vol. 53, Issue 3, (Dec. 31, 2001).
Yurong Yang Wheeler, et al., "Intrabody and Intrakine Strategies for Molecular Therapy", Molecular Therapy, vol. 8, Issue 3, pp. 355-366, (Sep. 2003).
Roland E. Kontermann, "Intrabodies as therapeutic agents", Methods, vol. 34, Issue 2, pp. 163-170, (Oct. 2004).
Eric Tse, et al., "Intracellular antibody-caspase-mediated cell killing: An approach for application in cancer therapy", Proceedings of the National Academy of Sciences of the United States of America, vol. 97, Issue 22, pp. 12266-12271, (Oct. 24, 2000).
Boon Chin Heng, et al., "Making cell-permeable antibodies (Transbody) through fusion of protein transduction domains (PTD) with single chain variable fragment (scFv) antibodies: Potential advantages over antibodies expressed within the intracellular environment (Intrabody)", Medical Hypotheses, vol. 64, Issue 6, pp. 1105-1108, (2005).
Lilly Y. W. Bourguignon, et al., "CD44 Interaction with Tiam1 Promotes Rac1 Signaling and Hyaluronic Acid-mediated Breast Tumor Cell Migration", The Journal of Biological Chemistry, vol. 275, Issue 3, pp. 1829-1838, (Jan. 21, 2000).
Y. Matsubara, et al., "Expression of CD44 Variants in Lung Cancer and Its Relationship to Hyaluronan Binding", The Journal of International Medical Research, vol. 28, Issue 2, pp. 78-90, (2000).
Takeshi Shimizu, et al., "Nanogel DDS enables sustained release of IL-12 for tumor immunotherapy", Biochemical and Biophysical Research Communications, vol. 367, Issue 2, pp. 330-335, (Mar. 7, 2008).
Kelly R. Kirker, et al., "Glycosaminoglycan hydrogel films as biointeractive dressings for wound healing", Biomaterials, vol. 23, Issue 17, pp. 3661-3671, (Sep. 2002).
Tushar Kanti Maiti, et al., "Interaction of (−)-Epigallocatechin-3-Gallate With Human Serum Albumin: Fluorescence, Fourier Transform Infrared, Circular Dichroism, and Docking Studies", Proteins: Structure, Function, and Bioinformatics, vol. 64, Issue 2, pp. 355-362, (Aug. 1, 2006).
Ikuro Abe, et al., "Antioxidative galloyl esters as enzyme inhibitors of p-hydroxybenzoate hydroxylase", FEBS Letters, vol. 483, Issues 2-3, pp. 131-134, (Oct. 20, 2000).
Harshadrai M. Rawel, et al., "Determining the binding affinities of phenolic compounds to proteins by quenching of the intrinsic tryptophan fluorescence", Molecular Nutrition & Food Research, vol. 50, Issue 8, pp. 705-713, (Aug. 2006).
Florian C. Kurschus, et al., "Killing of target cells by redirected granzyme B in the absence of perforin", FEBS Letters, vol. 562, Issues 1-3, pp. 87-92, (Mar. 26, 2004).
Tracy Zordan-Nudo, et al., "Effects of Nonionic Detergents on P-Glycoprotein Drug Binding and Reversal of Multidrug Resistance", Cancer Research, vol. 53, Issue 24, pp. 5994-6000, (Dec. 15, 1993).
Jerzy Jankun, et al., "Why drinking green tea could prevent cancer", Nature, vol. 387, No. 6633, p. 561, (Jun. 5, 1997).
Alessandra Bordoni, et al., "Green tea protection of hypoxia/reoxygenation injury in cultured cardiac cells", The Journal of Nutritional Biochemistry, vol. 13, Issue 2, pp. 103-111, (Feb. 2002).
Kiyotaka Nakagawa, et al., "Tea Catechin Supplementation Increases Antioxidant Capacity and Prevents Phospholipid Hydroperoxidation in Plasma of Humans", Journal of Agricultural and Food Chemistry, vol. 47, Issue 10, pp. 3967-3973, (1999).
Junji Terao, et al., "Protective Effect of Epicatechin, Epicatechin Gallate, and Quercetin on Lipid Peroxidation in Phospholipid Bilayers", Archives of Biochemistry and Biophysics, vol. 308, Issue 1, pp. 278-284, (Jan. 1994).
Mamoru Isemura, et al., "Tea catechins and related polyphenols as anti-cancer agents", BioFactors, vol. 13, Nos. 1-4, pp. 81-85, (2000).
Ikuo Ikeda, et al., "Tea Catechins with a Galloyl Moiety Suppress Postprandial Hypertriacylglycerolemia by Delaying Lymphatic Transport of Dietary Fat in Rats", The Journal of Nutrition, vol. 135, Issue 2, pp. 155-159, (Feb. 2005).
Gereon Lill, et al., "Complex effects of different green tea catechins on human platelets", FEBS Letters, vol. 546, Issues 2-3, pp. 265-270, (Jul. 10, 2003).
Senji Sakanaka, et al., "Inhibitory Effects of Green Tea Polyphenols on the Production of a Virulence Factor of the Periodontal-Disease-Causing Anaerobic Bacterium *Porphyromonas gingivalis*", vol. 52, No. 6, pp. 1688-1692, (Mar. 24, 2004).
Takako Yokozawa, et al., "Antioxidative Activity of Green Tea Treated with Radical Initiator 2,2'-Azobis(2-amidinopropane) Dihydrochloride", Journal of Agricultural and Food Chemistry, vol. 48, No. 10, pp. 5068-5073, (Oct. 2000).
Spiridione Garbisa, et al., "Tumor invasion: molecular shears blunted by green tea", Nature Medicine, vol. 5, Issue 11, p. 1216, (1999).
Hirofumi Tachibana, et al., "A receptor for green tea polyphenol EGCG", Nature Structural & Molecular Biology, vol. 11, Issue 4, pp. 380-301, (Apr. 2004).
Dale G. Nagle, et al., "Epigallocatechin-3-gallate (EGCG): Chemical and biomedical perspectives", Phytochemistry, vol. 67, Issue 17, pp. 1849-1855, (Sep. 2006).
Shengmin Sang, et al., "Autoxidative quinine formation in vitro and metabolite formation in vivo from tea polyphenol (-)-epigallocatechin-3-gallate: Studied by real-time mass spectrometry combined with tandem mass ion mapping", Free Radical Biology and Medicine, vol. 43, Issue 3, pp. 362-371, (Aug. 1, 2007).
Chung S. Yang, et al., "Tea and Cancer", Journal of the National Cancer Institute, vol. 85, Issue 13, pp. 1038-1049, (Jul. 7, 1993).
Spiridione Garbisa, et al., "Tumor Gelatinases and Invasion Inhibited by the Green Tea Flavanol Epigallocatechin-3-Gallate", Cancer, vol. 91, No. 4, pp. 822-832, (Feb. 15, 2001).
Ge Jiang, et al., "Target Specific Intracellular Delivery of siRNA/PEI-HA Complex by Receptor Mediated Endocytosis", Molecular Pharmaceutics, vol. 6, Issue 3, pp. 727-737, (Jun. 1, 2009).
Hyukjin Lee, et al., "Target-specific intracellular delivery of siRNA using degradable hyaluronic acid nanogels", Journal of Controlled Release, vol. 119, Issue 2, pp. 245-252, (Jun. 1, 2007).
Christopher J. Froelich, et al., "New Paradigm for Lymphocyte Granule-mediated Cytotoxicity: Target Cells Bind and Internalize Granzyme B, but an Endosomolytic Agent is Necessary for Cytosolic Delivery and Subsequent Apoptosis," The Journal of Biological Chemistry, vol. 271, Issue 46, pp. 29073-29079, (Nov. 15, 1996).
EPO Communication enclosing Extended European Search Report for corresponding European Patent Application No. 10808429.4, 4 pages, (Dec. 3, 2012).

* cited by examiner

PARTICULATE HYALURONIC ACID/FLAVONOID SUSPENSIONS FOR CELLULAR DELIVERY OF BIOACTIVE AGENTS

CROSS-REFERENCE TO RELATED APPLICATIONS

This patent application is a U.S. National Phase application under 35 U.S.C. §371 of International Application No. PCT/SG2010/000,297, filed on Aug. 11, 2010, entitled PARTICULATE HYALURONIC ACID FORMULATIONS FOR CELLULAR DELIVERY OF BIOACTIVE AGENTS, which claims benefit of, and priority from, Singapore patent application No. 200905341-4 filed on Aug. 11, 2009, the contents of which are fully incorporated herein by reference.

FIELD OF THE INVENTION

The present invention relates generally to a suspension of immiscible particles in a solution, wherein the particles comprise an agglomeration of a bioactive agent and a plurality of conjugates of a hyaluronic acid and a flavonoid; wherein the particles are on average from about 15 nm to about 300 nm in diameter and wherein the bioactive agent is releasably retained in the particles by the flavonoid.

The present invention also relates to a therapeutic formulation comprising the suspension and methods for using the suspension and therapeutic formulation.

BACKGROUND OF THE INVENTION

A main challenge in cancer therapy is the selective delivery of cytotoxic agents to tumor cells. These cytotoxic agents can be small molecules or macromolecules (e.g. proteins, DNA and siRNA), and can have either extracellular or intracellular targets. Much research in cancer therapy has focused on improving the targeted delivery of small molecule drugs such as doxorubicin, which generally have poor selectivity to tumor cells.

More recently, the use of monoclonal antibodies such as Herceptin to specifically target tumor cells that overexpress the cell-surface Her2 receptor has emerged as a viable strategy to achieve targeted cancer therapy.[1,2] Monoclonal antibodies that are used today generally target extracellular receptors. However, there is a wide range of intracellular proteins in cancer cells that can be targeted by antibodies with intracellular targets, otherwise known as intrabodies.[3,4] An intrabody conjugated to caspase 3 which triggers apoptosis upon antibody-antigen interaction is a prime example of a potential intrabody-based cancer therapy.[5]

Some common methods of delivering intrabodies are: (i) the transfection of recombinant DNA coding the intrabody into cancer cells, resulting in intracellular expression of the intrabody, and (ii) the fusion of protein transduction domains to the intrabody to make it more cell-permeable.[6] The first method usually requires the use of viral vectors, which raise safety concerns for human clinical use. Furthermore, protein folding and stability of the expressed intrabody in the successfully transfected cancer cells may be affected by the reducing intracellular environment. In the second method, the intrabody protein being delivered is not protected from degradation, and is even modified to include a transduction domain, which may compromise intrabody activity and hence its intracellular function. Neither of theses existing methods enable the active targeting of tumor cells, which is important to minimize any side effects of the intrabody being delivered.

SUMMARY OF INVENTION

In one aspect, there is presently provided a suspension of immiscible particles in a solution, wherein the particles comprise an agglomeration of a bioactive agent and a plurality of conjugates of a hyaluronic acid and a flavonoid; wherein the particles are on average from about 15 nm to about 300 nm in diameter and wherein the bioactive agent is releasably retained in the particles by the flavonoid. In another aspect there is provided a therapeutic formulation comprising the suspension as describe herein. The suspension and therapeutic formulation may be used to deliver the bioactive agent to cells, including cancer cells.

Thus in one aspect there is provided a suspension of immiscible particles in a solution, wherein the particles comprise an agglomeration of a bioactive agent; and a plurality of conjugates of a hyaluronic acid and a flavonoid; wherein the particles are on average from about 15 nm to about 300 nm in diameter and wherein the bioactive agent is releasably retained in the particles by the flavonoid.

In particular embodiments, the solution is an aqueous solution.

In different particular embodiments, the bioactive agent is releasably retained in the particles by a hydrophobic bond between the flavonoid and the bioactive agent or by an ionic bond between the flavonoid and the bioactive agent.

In particular embodiments, the particles are on average from about 50 nm to about 100 nm in diameter.

In certain embodiments, the flavonoid is a catechin-based flavonoid, including for example epigallocatechin gallate.

In particular embodiments, the bioactive agent is an anti-cancer agent.

In different embodiments, the bioactive agent is a protein, including for example an intrabody or Granzyme B.

In certain embodiments, the bioactive agent is a bioactive agent that is incapable of entering into a cell when delivered to the cell alone.

In particular embodiments, the HA has a molecular weight of from about 5000 to about 10000000 daltons.

In particular embodiments, there is provided the suspension as described herein wherein the particles are formed by combining in a solution 0.01% w/v to about 1.0% w/v of a bioactive agent and 0.05 µg/ml to about 5000 µg/ml of conjugates of a hyaluronic acid and a flavonoid.

In certain embodiments, the particles of the suspension as described herein further comprise an endosomolytic agent, including for example polyethylenimine.

In another aspect, there is provided a therapeutic formulation comprising the suspension as described herein.

In yet another aspect, there is provided a method for delivery of a bioactive agent to a cell, the method comprising contacting the cell with the suspension or formulation as described herein.

In another aspect, there is provided a method for intracellular delivery of a bioactive agent to a cell, the method comprising contacting the cell with the suspension or formulation as described herein.

In particular embodiments of the method for delivery of a bioactive agent to a cell and the method for intracellular delivery of a bioactive agent to a cell described herein, the cell is a cancer cell.

In different embodiments of the method for delivery of a bioactive agent to a cell and the method for intracellular delivery of a bioactive agent to a cell described herein, the cell is in vitro or in vivo. In one embodiment, the method comprises administering the particle to a subject in an amount effective for the treatment of cancer.

In other aspects, there is provided use of the suspension or formulation as described herein for delivery of a bioactive agent to a cell and in the manufacture of a medicament for delivery of a bioactive agent to a cell.

In another aspect there is provided, the suspension or formulation as described herein for use in the delivery of a bioactive agent to a cell.

In other aspects, there is provided use of the suspension or formulation as described herein for intracellular delivery of a bioactive agent to a cell and in the manufacture of a medicament for intracellular delivery of a bioactive agent to a cell.

In another aspect, there is provided the suspension or formulation as described herein for use in the intracellular delivery of a bioactive agent to a cell.

In particular embodiments of the uses, suspension or formulation as described herein, the cell is a cancer cell.

In one embodiment, the use, suspension or formulation as described is in an amount effective for the treatment of cancer.

In another aspect, there is presently provided a method of formulating a suspension of immiscible particles comprising combining in a solution 0.01% w/v to about 1.0% w/v of a bioactive agent; and 0.05 μg/ml to about 5000 μg/ml of conjugates of a hyaluronic acid and a flavonoid; to form the suspension of particles wherein the particles comprise an agglomeration of the bioactive agent and the conjugates of hyaluronic acid and a flavonoid, wherein the particles are on average from about 15 nm to about 300 nm in diameter and wherein the bioactive agent is releasably retained in the particles by the flavonoid.

In particular embodiments of the present method of formulating a suspension of immiscible particles, the solution is an aqueous solution.

In different particular embodiments, the bioactive agent is releasably retained in the particles by a hydrophobic bond between the flavonoid and the bioactive agent or by an ionic bond between the flavonoid and the bioactive agent.

In particular embodiments, the particles are on average from about 50 nm to about 100 nm in diameter.

In certain embodiments of the present method of formulating a suspension of immiscible particles, the flavonoid is a catechin-based flavonoid, including for example epigallocatechin gallate.

In particular embodiments, the bioactive agent is an anticancer agent.

In different embodiments, the bioactive agent is a protein, including for example an intrabody or Granzyme B.

In certain embodiments of the present method of formulating a suspension of immiscible particles, the bioactive agent is a bioactive agent that is incapable of entering into a cell when delivered to the cell alone.

In particular embodiments, the HA has a molecular weight of from about 5000 to about 10000000 daltons.

In certain embodiments, the present method of formulating a suspension of immiscible particles comprises combining an endosomolytic agent with the bioactive agent and the conjugates of a hyaluronic acid and a flavonoid to form the suspension and wherein the particles further comprise the endosomolytic agent. In particular embodiments, the endosomolytic agent is polyethylenimine.

In particular embodiments, the present method of formulating a suspension of immiscible particles is to formulate a therapeutic formulation.

In another aspect, there is provided a method of treating a disease comprising administering to a subject in need thereof an effective amount of the suspension or formulation as described herein. In certain embodiments, the disease is cancer.

BRIEF DESCRIPTION OF THE DRAWINGS

In the figures, which illustrate, by way of example only, embodiments of the present invention.

DETAILED DESCRIPTION

Figure 1:
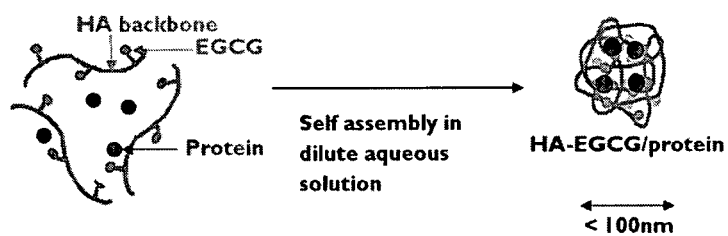
FIG. 1. Self-assembly of HA-EGCG and protein into a particle.

In one aspect, there is provided a suspension of immiscible particles in a solution, wherein the particles comprise an agglomeration of a bioactive agent; and a plurality of conjugates of a hyaluronic acid and a flavonoid; wherein the particles are on average from about 15 nm to about 300 nm in diameter and wherein the bioactive agent is releasably retained in the particles by the flavonoid.

As used herein, suspension refers to a heterogeneous mixture in which particles are dispersed throughout a medium, preferably a liquid. As would be understood, the particles of a suspension may settle out of the medium but can be re-dispersed, for example through agitation of the mixture. As used herein, suspension is not restricted to mixtures comprising particles with a diameter greater than one micrometer but encompasses mixtures comprising particles with diameters of less than one micrometer including particles with a diameter between 15 and 300 nm.

As used herein, agglomeration refers to a mixture or aggregation of molecules, moieties or compounds.

The presently described particles may provide delivery of the bioactive agent contained in the particles to cells. Furthermore, the presently described particles may provide targeted delivery of the bioactive agent contained in the particles to cancer cells. The inclusion of hyaluronic acid (HA) in the present particles provides an active targeting sequence for the CD44 receptor that binds HA and is overexpressed in many cancer cell types including colon, breast, ovarian, liver and pancreas cancer cells.[7, 8] As such, the particles presently provided may specifically target cancer cells that overexpress the CD44 receptor for delivery of the bioactive agent. In particular embodiments, the bioactive agent is an anti-cancer agent.

Flavonoids, such as (−)-epigallocatechin gallate (EGCG) have the ability to bind proteins,[11, 12] through the formation of non-covalent reversible bonds such as ionic or hydrophobic bonds. Thus, in the presently described particles, the bioactive agent may be releasably retained in the particles by interactions between the flavonoid and the bioactive agent including non-covalent bonds such as hydrophobic, hydrogen or ionic bonds. Use of such non-covalent binding to retain the bioactive agent in the particles avoids the need for chemical conjugation which can irreversibly alter the tertiary structure of the bioactive agent and thus its activity. Furthermore, such non-covalent bonds, while retaining the bioactive agent in the particles when the particles are in the presently described suspension, may allow for release of the bioactive agent from the particles to be easily achieved upon delivery of the bioactive agent to a cell.

Thus, in one embodiment of the present suspension, the bioactive agent is releasably retained in the particles by the flavonoid. In specific embodiments, the bioactive agent is releasably retained in the particles through non-covalent bonds between the bioactive agent and the flavonoid. In different embodiments, the non-covalent bonds may be hydrophobic bonds, ionic bonds or hydrogen bonds. In certain embodiments, the non-covalent bonds between the flavonoid and the bioactive agent retain the bioactive agent in the particles when in the present suspension but release the bioactive agent from the particles following delivery of the bioactive agent to a cell.

In particular embodiments, the bioactive may have an affinity for the flavonoid such that the bioactive agent preferentially interacts or binds with the flavonoid over other compounds, molecules or components. For example, the bioactive agent may have a higher affinity for the flavonoid than for the HA. Thus, in certain embodiments, the bioactive agent may preferentially, but, releasably interact with the flavonoid such that the bioactive agent is preferentially retained in the particle As used herein, "releasably retained" refers to retainment of the bioactive agent in the present particles in such a manner that the bioactive agent may be subsequently released from the particles. In certain embodiments, the bioactive agent is released from the particles by disruption of interactions, including for example non-covalent bonds, between the flavonoid and the bioactive agent.

In certain embodiments, the interaction between the flavonoid and the bioactive agent in the present particles may be characterized by complexation between the flavonoid and the bioactive agent such that the flavonoid and the bioactive agent interact to form a complex. As used herein a "complex" refers to an entity formed from association of components through specific interactions rather than random association of the components. As would be understood by a skilled person, a complex may be comprised of different types of interactions but that the interactions included within a particular complex are limited to certain specific types of interactions that are defined by the components or parts of the components that are involved in the interaction as well the types of interactions or bonds formed. Thus, in particular embodiments, in the presently described particles the bioactive agent and the plurality of conjugates of a HA and a flavonoid form a complex.

The particles presently provided are formed by the self-assembly of the conjugates of HA and a flavonoid (HA-flavonoid conjugates) and the bioactive agent to form the particles as presently described (FIG. 1). Without being limited to any particular theory, the self-assembly of HA-flavonoid conjugates and the bioactive agent into the presently provided particles may result from the interactions between the flavonoid and the bioactive agent. In particular embodiments, the self-assembly of HA-flavonoid conjugates and the bioactive agent into the presently provided particle may result from the formation of reversible non-covalent binding between the flavonoid and the bioactive agent.

Without being limited to any particular theory, it appears that in contrast to a polymeric or liposomal carrier, the present particles provide a hydrated environment within the particles, which can protect the bioactive agent from degradation, including degradation by proteases or the reticulo-endothelial system, hence providing an extended circulation time for the bioactive agent. Furthermore, the use of HA-flavonoid conjugates to form the present particles may reduce potential biocompatibility concerns about delivery system materials as HA has been proven to be a biocompatible material.[10]

In particular embodiments, the presently described particles may be able enter or be transported into a cell and thus the present particles may deliver the bioactive agent directly inside a cell. Such direct delivery of the bioactive agent into the cell eliminates the need for viral transfection and intracellular expression. Furthermore, the present particles may provide delivery of the bioactive agent into a cell without the need to modify the bioactive agent, for example by adding a transduction domain, in order enable the bioactive agent to traverse the plasma membrane and enter the cell. In particular embodiments, the present particles may be used to deliver into a cell a bioactive agent that ordinarily cannot cross the cell plasma membrane when delivered to a cell on its own.

Thus the present particles may provide delivery of a bioactive agent to a cell and in certain embodiments, targeted delivery of a bioactive agent to a cancer cell. In particular embodiments, the present particles may provide delivery of the bioactive agent directly into the cell. The present particle may provide such delivery without modifications of the bioactive agent to incorporate targeting or transduction domains which can alter the functionality or activity of the bioactive agent.

Flavonoids are one of the most numerous and best-studied groups of plant polyphenols. The flavonoids'consist of a large group of low-molecular weight polyphenolic substances naturally occurring in fruits and vegetables, and are an integral part of the human diet. Dried green tea leaves can contain as much as 30% flavonoids by weight, including a high percentage of flavonoids known as catechins (flavan-3-ol derivatives or catechin-based flavonoids), including (−)-epicatechin, (−)-epigallocatechin, (+)-catechin, (−)-epicatech in gallate and (−)-epigallocatechin gallate.

In recent years, these green tea catechins have attracted much attention because they have been recognized to have biological and pharmacological properties, including antibacterial, anti-neoplastic, anti-thrombotic, vasodilatory, antioxidant, anti-mutagenic, anti-carcinogenic, anti-hypercholesterolemic, anti-viral and anti-inflammatory properties, which have been demonstrated in numerous human, animal and in vitro studies[16-18]. These biological and pharmacological properties are potentially beneficial in preventing diseases and protecting the stability of the genome. Many of the beneficial effects of catechins are thought to be linked to the antioxidant actions of the catechins[19]. Among the catechins, (−)-epigallocatechin gallate (EGCG), which is a major component of green tea, is thought to have the highest activity, possibly due to the trihydroxy B ring and the gallate ester moiety at the C3 position[20-24]. EGCG has been recognized to have biochemical and pharmaceutical effects including antioxidant, anti-carcinogenic, and anti-inflammatory properties[25-27]. EGCG is known to inhibit a vast array of biomedically relevant molecular targets and disease-related cellular process[28] consequently leading to the induction of apoptosis, inhibition of tumour cell growth, and inhibition of angiogenesis[29]. These beneficial bioactivities are attributed mostly to the strong binding ability of EGCG to many biological molecules, including peptides and proteins, which affect various enzyme activities and signal transduction pathways[30]. EGCG is also known as a potent inhibitor of matrix metalloproteinase (MMP) gelatinases[31] which play a crucial role in tumour metastasis.

Thus, in certain embodiments, if the bioactive agent included in the present particles has a therapeutic effect that is also provided by the flavonoid included in the present particles, then the present particles may provide therapeutic synergism due to combined delivery of the bioactive agent and the flavonoid to a cell. In one embodiment, the combination of an anti-cancer agent and a flavonoid, such as EGCG in the present particles may provide therapeutic syngergism in the treatement of cancer.

Formation of HA-Flavonoid Conjugates

The particles presently described are comprised of a bioactive agent, including an anti-cancer agent, and a plurality of conjugates of hyaluronic acid (HA) and a flavonoid (HA-flavonoid conjugates).

The HA-flavonoid conjugates of the present particles may be comprised of HA and any suitable flavonoid, as described below.

In different embodiments, the HA is aldehyde-derivatized hyaluronic acid, hyaluronic acid conjugated with aminoacetylaldehyde diethylacetal, or either of the aforementioned hyaluronic acid polymers derivatized with tyramine. Methods of synthesizing such HA polymers are known in the art and have been described for example in international application WO 2006/124000 and US application 2008/102052, the content of which are fully incorporated herein.

The free aldehyde group on the HA moiety allows for the conjugation of the HA in a controlled manner to either the C6 or the C8 position of the A ring, or both, of a flavonoid structure, thus preventing disruption of the flavonoid structure, particularly the B and C rings of the flavonoid, and thus preserving the beneficial biological and pharmacological properties of the flavonoid.

The flavonoid may be any flavonoid from the general class of molecules derived from a core phenylbenzyl pyrone structure, and includes flavones, isoflavones, flavonols, flavanones, flavan-3-ols, catechins, anthocyanidins and chalcones.

In particular embodiments the flavonoid is a catechin or a catechin-based flavonoid. A catechin, or a catechin-based flavonoid is any flavonoid that belongs to the class generally known as catechins (or flavan-3-ol derivatives), and includes catechin and catechin derivatives, including epicatechin, epigallocatechin, catechin, epicatechin gallate and epigallocatechin gallate, and including all possible stereoisomers of catechins or catechin-based flavonoids. In particular embodiments, the catechin-based flavonoid is (+)-catechin or (−)-epigallocatechin gallate. In a particular embodiment, the catechin-based flavonoid is epigallocatechin gallate (EGCG).

A catechin-based flavonoid to be conjugated to HA may be a single monomeric unit of a catechin-based flavonoid or it may be an oligomer of one or more catechin-based flavonoids. The conjugation of HA to a flavonoid can result in augmentation of the flavonoid's biological or pharmacological properties. Furthermore, oligomers of catechin-based flavonoids tend to have amplified or augmented levels of the biological and pharmacological properties associated with catechin-based flavonoids, and may even have reduced pro-oxidant effects that are sometimes associated with monomeric catechin-based flavonoids. Thus in one embodiment, an oligomerized catechin-based flavonoid having amplified or augmented flavonoid properties is conjugated to HA.

Oligomers of catechin-based flavonoids that can be conjugated to HA, such as polymers, are known, and include oligomers prepared through enzyme-catalyzed oxidative coupling and through aldehyde-mediated oligomerization, for example as described in published international application WO 2006/124000 and published US application 2008/102052, the contents of which are fully incorporated by reference herein.

An aldehyde-mediated oligomerization process results in an unbranched oligomer that has defined linkages, for example through carbon-carbon linkages such as $CH-CH_3$ bridges linked from the C6 or C8 position on the A ring of one monomer to the C6 or C8 position on the A ring of the next monomer, including in either possible stereoconfiguration, where applicable. Thus, the $CH-CH_3$ linkage may be between the C6 position of the A ring of one monomer and either of the C6 or C8 position of the next monomer or it may be between the C8 position of the A ring of the first monomer and either of the C6 or C8 position of the next monomer.

The oligomer of catechin-based flavonoid to be conjugated to HA, for example a polymer, may be of 2 or more monomeric units linked together. In certain embodiments, the catechin-based flavonoid oligomer has from 2 to 100 monomer units, from 10 to 100, from 2 to 80, from 10 to 80, from 2 to 50, from 10 to 50, from 2 to 30, from 10 to 30, from 20 to 100, from 30 to 100 or from 50 to 100 monomeric units.

HA may be conjugated to the flavonoid by any suitable means known in the art that provides attachment of HA to the flavonoid to form a conjugate capable of being formed into particles as described herein without disruption of the polyphenol structure of the flavonoid.

In one embodiment, HA may be conjugated to a flavonoid by "aldehyde mediated conjugation" wherein HA is reacted with the flavonoid in the presence of an acid catalyst, the HA moiety having a free aldehyde group, or a group that is able to be converted to a free aldehyde group in the presence of acid. Aldehyde-mediated conjugation of HA to a flavonoid can result in attachment of HA at the C6 and/or C8 position of the flavonoid A ring, which does not disrupt or affect the B and C rings of the flavonoid or the various hydroxyl groups on the flavonoid. Formation of HA-flavonoid conjugates by aldehyde mediated conjugation is described in published international application WO 2006/124000 and published US application 2008/102052, the contents of which are fully incorporated by reference herein.

In other embodiments, the flavonoid to be conjugated to the HA may be modified to form a flavonoid derivative that comprises a functional group that is suitable for conjugation with the HA. In particular embodiments, the flavonoid is modified to form a flavonoid derivative that comprises a terminal group that is suitable for conjugation with the HA. In different embodiments, the flavonoid may be modified to comprise a carboxyl, an amine or a succinimide functional group. Thus in particular embodiments, the HA-flavonoid conjugate may be formed by first preparing a flavonoid derivative comprising a functional group, for example a terminal group, suitable for conjugation with HA. This flavonoid derivative is then reacted with HA to form the HA-flavonoid conjugate.

In a particular embodiment, the HA-flavonoid conjugate is comprised of HA conjugated to a catechin-based flavonoid and the conjugation is carried out by aldehyde mediated conjugation as defined above. Thus, the conjugation reaction may involve conjugation of a HA moiety containing a free aldehyde group or a group that is able to be converted to a free aldehyde group in the presence of acid to a catechin-based flavonoid. Thus in one embodiment, the HA-flavonoid conjugate may be synthesized using acid catalysis of a condensation of the aldehyde group of HA with a catechin-based flavonoid, or using acid to convert a functional group on HA to a free aldehyde prior to condensation of the aldehyde group with the catechin-based flavonoid. In a particular embodiment, the catechin-based flavonoid is EGCG.

To conjugate HA and the flavonoid, the HA moiety and the flavonoid may be separately dissolved in a suitable solvent. For example, HA with the free aldehyde may be added by dropwise addition, to a solution containing the flavonoid, in the presence of an acid, for example at a pH from about 1 to about 5, or for example at pH of about 1. The reaction is allowed to go to completion. Following the conjugation reaction, excess unreacted flavonoid can be removed from the conjugated composition, for example by dialysis or by molecular sieving.

In another embodiment, the HA moiety may be dissolved in deionized or distilled water and mixed with a solution comprising the flavonoid dissolved in dimethyl sulfoxide (DMSO). The pH of the solution is adjusted to about 1 by addition of an acid, for example HCl and the reaction is allowed to go to completion, for example by stirring at room temperature for about 24 hours. Following the conjugation reaction, the conjugate may be purified from the solution, for example by dialysis.

The ratio of flavonoid to HA, may be varied, so that there is only one HA moiety attached to the flavonoid, or so that there is a flavonoid attached at more than one position on the HA moiety or so that the flavonoid has two HA moieties attached, for example one at either of the C6 and C8 positions of a catechin-based flavonoid.

The ratio of HA moiety to flavonoid in the conjugate can be controlled through the ratio of starting reagents. For example, when the molar ratio of HA to flavonoid is about 1, a single HA moiety will be attached to a single flavonoid moiety (either monomeric or oligomeric may be used). However, at higher concentrations of HA, for example at a 10:1 molar ratio of HA to flavonoid, a composition having a tri-block structure of HA-flavonoid-HA may be obtained.

Similarly, the degree of conjugation of HA with the flavonoid can be varied by varying the concentrations of HA and flavonoid in the conjugation reaction. The "degree of conjugation" as used herein refers to the number of flavonoid molecules per 100 units of HA. For example, a 50% degree of conjugation means that there are 50 flavonoid molecules per 100 units of HA.

Since HA has multiple sites that may react with a flavonoid during the conjugation reaction, by varying the concentration of the flavonoid in the starting reaction, it is possible to vary the degree of conjugation between HA and the flavonoid.

The ratio of HA to flavonoid in the starting reagents for forming the HA-flavonoid conjugates may be varied to adjust the degree of conjugation of the HA with the flavonoid in the resulting HA-flavonoid conjugates and thus the ratio of HA to flavonoid present in a particle formed from these HA-flavonoid conjugates.

In a particular embodiment, the HA-flavonoid conjugate is a conjugate of HA and EGCG and the conjugate is synthesized in a two-step procedure. In the first step protected aldehyde groups are introduced to HA by conjugating diethoxyethyl amine (DA) to HA though NHS/EDC chemistry for form HA-DA conjugates. The HA-EGCG conjugate is then formed by deprotection of the HA-DA conjugates at a pH of 1 to allow conjugation of EGCG to the aldehyde groups.

In different embodiments, the HA moiety has a molecular weight of from about 5000 to about 10,000,000 daltons, at least about 5000 daltons, at least about 10,000 daltons, at least about 20,000 daltons, at least about 30,000 daltons, at least about 40,000 daltons, at least about 50,000 daltons, at least about 60,000 daltons, at least about 70,000 daltons, at least about 80,000 daltons, at least about 90,000 daltons, at least about 100,000 daltons, at least about 150,000 daltons, at least about 200,000 daltons, at least about 250,000 daltons, at least about 300,000 daltons, at least about 350,000 daltons, at least about 400,000 daltons, at least about 450,000 daltons, at least about 500,000 daltons, at least about 550,000 daltons, at least about 600,000 daltons, at least about 650,000 daltons, at least about 700,000 daltons at least about 750,000 daltons, at least about 800,000 daltons, at least about 850,000 daltons, at least about 900,000 daltons, at least about 950,000 daltons, at least about 1,000,000 daltons, at least about 1,500,000 daltons, at least about 2,000,000 daltons, at least about 2,500,000 daltons, at least about 3,000,000 daltons, at least about 3,500,000 daltons, at least about 4,000,000 daltons, at least about 4,500,000 daltons, at least about 5,000,000 daltons, at least about 5,500,000 daltons, at least about 6,000,000 daltons, at least about 6,500,000 daltons, at least about 7,000,000 daltons, at least about 7,500,000 daltons, at least about 8,000,000 daltons, at least about 8,500,000 daltons, at least about 9,000,000 daltons, at least about 9,500,000 daltons, or at least about 10,000,000 daltons.

Formation of Particles Comprising HA-Flavonoid Conjugates and a Bioactive Agent

In one aspect, there is presently provided a suspension of immiscible particles in an solution, wherein the particles comprise an agglomeration of a bioactive agent; and a plurality of conjugates of a hyaluronic acid and a flavonoid; wherein the particles are on average from about 15 nm to about 300 nm in diameter and wherein the bioactive agent is releasably retained in the particles by the flavonoid.

The solution may be any solution that is suitable for dispersion of the presently described particles to form the present suspension. The solution is preferably non-toxic and suitable for pharmacological use. In one embodiment, the solution is an aqueous solution.

The bioactive agent may be any agent that has a biological, pharmacological or therapeutic effect in a body or cell, and includes without limitation a protein, a nucleic acid, a small molecule or a drug. A bioactive agent that is a protein may be for example a peptide, an antibody, an intrabody, a hormone, an enzyme, a growth factor or a cytokine. A bioactive agent that is a nucleic acid may be for example single stranded or double stranded DNA or RNA, a short hairpin RNA, an siRNA, or may comprise a gene encoding a therapeutic product. Also included in the scope of bioactive agent are antibiotics, chemotherapeutic agents, antihypertensive agents, anti-cancer agents, anti-bacterial agents, anti-neoplastic agents, anti-thrombotic agents, vasodilatory agents, anti-oxidants, anti-mutagenic agents, anti-carcinogenic agents, anti-hypercholesterolemic agents, anti-viral agents and anti-inflammatory agents.

In particular embodiments, the bioactive agent delivered into the cell may be an agent that is unable to traverse the plasma membrane and enter the cell when delivered to the cell on its own. For example, some agents may be unable to traverse the plasma membrane on their own due to their size, hydrophobicity, hydrophilicity or charge.

In particular embodiments, the bioactive agent may be an anti-cancer agent. As used herein, "anti-cancer agent" refers to any agent that has a biological, pharmacological or therapeutic effect in a body for the treatment of cancer or that has an anti-cancer effect on a cell, including an anti-tumour effect, such as a cytotoxic, apoptotic, anti-mitotic anti-angiogenesis or inhibition of metastasis effect. "Anti-cancer effect" as used herein is intended to include inhibition or reduction of tumour cell growth, inhibition or reduction of carcinogenesis, killing of tumour cells, or inhibition or reduction of carcinogenic or tumourogenic properties of a cell, including a tumour cell.

In particular embodiments, the anti-cancer agent may be for example a peptide, an antibody, an intrabody, an enzyme or a cytotoxic protein. In particular embodiments, the anti-cancer agent is an intrabody or Granzyme B. Also included in the scope of an anti-cancer agent are chemotherapeutic agents, anti-cancer agents, anti-neoplastic agents, anti-oxidants, anti-mutagenic agents and anti-carcinogenic agents.

The anti-cancer agent may be, for example, herceptin, TNP470, trastuzumab, bevacizumab, rituximab, erlotinib, daunorubicin, doxorubicin, etoposide, vinblastine, vincristine, pacitaxel, methotrexate, 5-fluorouracil, gemcitabine, arabinosylcytosine, altretamine, asparaginase, bleomycin, capecitabine, carboplatin, carmustine, BCNU, cladribine, cisplatin, cyclophosphamide, cytarabine, dacarbazine, dactinomycin, actinomycin D, docetaxel, doxorubicin, doxorubicin, imatinib, doxorubicin liposomal, VP-16, fludarabine, gemcitabine, hydroxyurea, idarubicin, ifosfamide, irinotecan, CPT-11, methotrexate, mitomycin, mitotane, mitoxantrone, topotecan, vinblastine, vincristine, vinorelbine or an antibody for use in immunotherapy.

References herein to embodiments that include a bioactive agent are meant to exemplify, in addition, embodiments in which an agent, such as a non-bioactive agent, is substituted for the bioactive agent. Thus, in particular embodiments there is presently provided a suspension of immiscible particles in a solution, wherein the particles comprise an agglomeration of an agent; and a plurality of conjugates of a hyaluronic acid and a flavonoid; wherein the particles are on average from about 15 nm to about 300 nm in diameter and wherein the agent is releasably retained in the particles by the flavonoid. As used herein "agent" may be a bioactive agent or a non-bioactive agent. As used herein "a non-bioactive agent" refers to an agent that does not have a biological, pharmacological or therapeutic effect in a body or cell and includes without limitation a protein, a nucleic acid or a small molecule that does not have a biological, pharmacological or therapeutic effect in a body or cell. Thus, in one embodiment the presently provided particles may comprise an agent that is a non-bioactive agent. In a particular embodiment, the agent is an inert compound, such as an inert marker for identifying particular cells in a cell population.

As described above, the present particles are formed by the self-assembly of a plurality of HA-flavonoid conjugates and the bioactive agent to form the particles as presently described.

To form the particles presently described, the HA-flavonoid conjugates are mixed with the bioactive agent in suitable reaction conditions and at suitable concentrations of the HA-flavonoid conjugates and bioactive agent to self-assemble to form the presently described particles that are from about 15 nm to about 300 nm.

The formation of the present particles is dependent on both the concentration of HA-flavonoid conjugates and the concentration of the bioactive agent which both may effect the self-assembly of the HA-flavonoid conjugates and the bioactive agent and the size of the particles formed.

To form the present particles, the HA-flavonoid conjugates are generally provided at concentrations an order of magnitude less then the concentrations that result in formation of the HA-flavonoid conjugates into a hydrogel. In different embodiments, the concentration of HA-flavonoid conjugates may be from about 0.05 µg/ml to about 5000 µg/ml, from about 10 µg/ml to about 5000 µg/ml, from about 10 µg/ml to about 1000 µg/ml, at least about 0.05 µg/ml, at least about 0.1 µg/ml, at least about 0.5 µg/ml, at least about 1 µg/ml, at least about 5 µg/ml, at least about 10 µg/ml, at least about 20 µg/ml, at least about 30 µg/ml, at least about 40 µg/ml, at least about 50 µg/ml, at least about 60 µg/ml, at least about 70 µg/ml, at least about 80 µg/ml, at least about 90 µg/ml, at least about 100 µg/ml, at least about 125 µg/ml, at least about 150 µg/ml, at least about 175 µg/ml, at least about 200 µg/ml, at least about 225 µg/ml, at least about 250 µg/ml, at least about 275 µg/ml, at least about 300 µg/ml, at least about 325 µg/ml, at least about 350 µg/ml, at least about 375 µg/ml, at least about 400 µg/ml, at least about 425 µg/ml, at least about 450 µg/ml, at least about 475 µg/ml, at least about 500 µg/ml, at least about 525 µg/ml, at least about 550 µg/ml, at least about 575 µg/ml, at least about 600 µg/ml, at least about 625 µg/ml, at least about 650 µg/ml, at least about 675 µg/ml, at least about 700 µg/ml, at least about 725 µg/ml, at least about 750 µg/ml, at least about 800 µg/ml, at least about 825 µg/ml, at least about 850 µg/ml, at least about 875 µg/ml, at least about 900 µg/ml, at least about 925 µg/ml, at least about 950 µg/ml, at least about 975 µg/ml, at least about 1000 µg/ml, at least about 1500 µg/ml, at least about 2000 µg/ml, at least about 2500 µg/ml, at least about 3000 µg/ml, at least about 3500 µg/ml, at least about 4000 µg/ml, at least about 4500 µg/ml or at least about 5000 µg/ml.

As discussed above, the formation of the present particles is also dependant on the concentration of the bioactive agent which can affect the self-assembly and size of the particles described herein. Increasing the concentration of the bioactive agent may increase or decrease the size of the particles formed. The effect of increasing the concentration of the bioactive agent may depend on the type of bioactive agent and the amount of bioactive agent used. For example, as demonstrated in FIG. 3 of the present application, at lower amounts of the bioactive agent an increase in the concentration of the bioactive agent can result in a reduction in the size of the particles formed whereas at higher amounts of the bioactive agent an increase in the concentration of the bioactive agent can result in an increase in the size of the particles formed.

In different embodiments, the concentration of the bioactive agent may be from about 0.01% w/v to about 1.0% w/v from about 0.1% w/v to about 0.75% w/v, at least about 0.01% w/v, at least about 0.02% w/v, at least about 0.03% w/v, at least about 0.04% w/v, at least about 0.05% w/v, at least about 0.06% w/v, at least about 0.07% w/v, at least about 0.08% w/v, at least about 0.09% w/v, at least about 0.1% w/v, at least about 0.15% w/v, at least about 0.2% w/v, at least about 0.25% w/v, at least about 0.3% w/v, at least about 0.35% w/v, at least about 0.4% w/v, at least about 0.45% w/v, at least about 0.5% w/v, at least about 0.55% w/v, at least about 0.6% w/v, at least about 0.65% w/v, at least about 0.7% w/v, at least about 0.75% w/v, at least about 0.8% w/v, at least about 0.85% w/v, at least about 0.90% w/v, at least about 0.95% w/v or at least about 1.0% w/v.

As would be understood by a skilled person, the concentration of the bioactive agent and the HA-flavonoid conjugates required to form the appropriate size particles to form the particles presently described may differ depending on the type of HA-flavonoid conjugates and type of bioactive agent. Furthermore, a skilled person would appreciate that the required concentrations of the bioactive agent and the HA-flavonoid conjugate to form the present particles may be relative to each other such that the required concentration of the bioactive agent may depend on the concentration of the HA-flavonoid conjugates and vice versa.

A person skilled in the art can use known methods and techniques to determine, based on the above factors, the relative concentrations of the bioactive agent and the HA-flavonoid conjugates required to form the appropriate size particles to form the particles presently described and thus the suspension and therapeutic formulation presently described.

Thus in one aspect, there is presently provided a method of formulating a suspension of immiscible particles comprising combining in a solution 0.01% w/v to about 1.0% w/v of a bioactive agent and 0.05 µg/ml to about 5000 µg/ml of conjugates of a hyaluronic acid and a flavonoid to form the suspension of particles wherein the particles comprise an agglomeration of the bioactive agent and the conjugates of hyaluronic acid and a flavonoid, wherein the particles are on average from about 15 nm to about 300 nm in diameter and wherein the bioactive agent is releasably retained in the particles by the flavonoid.

In contrast to larger structures, such as hydrogels, the size of the particles presently provided may allow for the particles to enter into cells, including cancer cells. Furthermore, the size of the present particles may provide increased mobility of the particles, as compared to larger structures, throughout the cell culture, body or extracellular environment that allows the particles to circulate and move between cells and towards target cancer cells.

As used herein "diameter" refers to hydrodynamic diameter as measured by dynamic light scattering. As would be understood by a skilled person, a "hydrodynamic diameter" refers to how a particle diffuses within a fluid. The diameter obtained by dynamic light scattering is that of a sphere that has the same translational diffusion coefficient as the particle being measured. In certain embodiments, the particles "diameter" may refer to or be referred to as the particles "apparent diameter" as the measured diameter may be a calculated average diameter based on one or more measurements of the physical properties of the particles.

In different embodiments, the present particles are on average from about 15 nm to about 300 nm, from about 50 to about 100 nm, at least about 15 nm, at least about 20 nm, at least about 25 nm, at least about 30 nm, at least about 35 nm, at least about 40 nm, at least about 45 nm, at least about 50 nm, at least about 55 nm, at least about 60 nm, at least about 65 nm, at least about 70 nm, at least about 75 nm, at least about 80 nm, at least about 85 nm, at least about 90 nm, at least about 95 nm, at least about 100 nm, at least about 125 nm, at least about 150 nm, at least about 175 nm, at least about 200 nm, at least about 225 nm, at least about 250 nm, at least about 275 nm or at least about 300 nm in diameter.

As discussed above, the present particles may be used to deliver the bioactive agent to a cell. In certain embodiments, the present particles may deliver the bioactive agent directly into a cell. In order for the particles to deliver the bioactive agent to a cell, the particles should be suitably sized to permit the particle to move through the cell culture, body or extracellular environment. In addition, if the bioactive agent is to be delivered into the cell, the particles should be suitably sized to permit entry of the particle into the cell. Thus, in particular embodiments, the present particles have an average diameter that permits the particles to move through a cell culture, body or extracellular environment or to enter into a cell.

A skilled person would be able to readily determine the size and stability of a particle using methods and techniques known in the art, including Dynamic Light Scattering as disclosed in the Examples below.

The present particles are immiscible. As used herein "immiscible" refers to particles that do not aggregate with other particles or additional HA-flavonoid conjugates or bioactive agents to form large particles or large aggregates substantially greater in size then the particles presently described. As would be understood by a skilled person, intermediate particles of less then about 300 nm may aggregate together in order to form the present particles. Such intermediate particles may be of different sizes. However, the present particles will not aggregate with each other to form particles that are on average greater than about 300 nm in diameter.

The present particles are stable in a solution. In particular embodiments, the present particles are stable in an aqueous solution. As used herein, a "stable" particle refers to a particle that remains immiscible and that does not disintegrate or dissolve in a solution, for example an aqueous solution, for a sufficient length of time for the intended use of the particles. For example, in one embodiment, the present particles may remain immiscible and will not disintegrate or dissolve in an aqueous solution for a sufficient amount of time to permit use of the presently described suspension or therapeutic agent for delivery of the bioactive agent to a cell. In another embodiment, the present particles may remain immiscible and will not disintegrate or dissolve in aqueous solution for a sufficient amount of time to permit storage of the presently described suspension or therapeutic formulation for a desired amount of time.

In different embodiments, the present particles are stable in a solution from at least about 1 hour to at least about 12 weeks, from at least about 1 day to at least about 7 days, from at least about 1 hour to at least about 24 hours, at least about 1 hour, at least about 2 hours, at least about 3 hours, at least about 4 hours, at least about 5 hours, at least about 6 hours, at least about 7 hours, at least about 8 hours, at least about 9 hours, at least about 10 hours, at least about 11 hours, at least about 12 hours, at least about 13 hours, at least about 14 hours, at least about 15 hours, at least about 16 hours, at least about 17 hours, at least about 18 hours, at least about 19 hours, at least about 20 hours, at least about 21 hours, at least about 22 hours, at least about 23 hours, at least about 24 hours, at least about 1 day, at least about 2 days, at least about, 3 days, at least about 4 day, at least about 5 days, at least about 6 days, at least about 7 days, at least about 1 week, at least about 2 weeks, at least about 3 weeks, at least about 4 weeks, at least about 5 weeks, at least about 6 weeks, at least about 7 weeks, at least about 8 weeks, at least about 9 weeks, at least about 10 weeks, at least about 11 weeks or at least about 12 weeks.

In a particular embodiment, the present particles further comprise an endosomolytic agent. Thus, in one embodiment, the present method of formulating a suspension of immiscible particles comprises combining an endosomolytic agent with the bioactive agent and the conjugates of a hyaluronic acid and a flavonoid to form the suspension and wherein the particles further comprise the endosomolytic agent.

As used herein "endosomolytic agent" refers to any agent that can mediate the release of particles from an endosome into the cytosol of a cell. For example, in particular embodiments, the endosomolytic agent may be polyethylenimine, melittin, an endosomolytic peptide or an endosomolytic protein.

In particular embodiments, the present particle may be transported into a cell through endocytosis. Without being limited to any particular theory, the transport of the present particle into a cell through endocytosis may be mediated by the binding of HA in the present particle to the CD44 receptor on the cell surface.

In endocytosis, particles are transported into the cell by internalization in endosomes which transport the particles from the cell surface into the cytosol. An endosomolytic agent may facilitate the release of the particles from the endosome into the cytosol by lysing the endosome.

As would be understood, when the bioactive agent of the present particles is an endosomolytic agent, for example an endosomolytic peptide or endosomolytic protein, it may not be necessary to include an additional endosomolytic agent.

The endosomolytic agent contained in the present particle is preferably non-toxic and suitable for pharmacological use. In particular embodiments, the activity of the endosomolytic agent is pH-sensitive and the endosomolytic agent is activated upon exposure to the low pH of the endosome.

In particular embodiments, the endosomolytic agent is polyethylenimine.

In a particular embodiment, there is presently provided a suspension of immiscible particles in an aqueous solution, wherein the particles comprise an agglomeration of a bioactive agent; and a plurality of conjugates of a hyaluronic acid and EGCG; wherein the particles are on average from about 15 nm to about 300 nm in diameter and wherein the bioactive agent is releasably retained in the particles by the EGCG as a result of the non-covalent bonds between the EGCG and the bioactive agent. In certain embodiments, the bioactive agent is releasably retained in the particles by hydrophobic bonds between the EGCG and the bioactive agent. In other embodiments, the bioactive agent is releasably retained in the particles by ionic bonds between the EGCG and the bioactive agent.

In another particular embodiment, there is presently provided a suspension of immiscible particles in an aqueous solution, wherein the particles comprise an agglomeration of a bioactive agent; and a plurality of conjugates of a hyaluronic acid and EGCG and an endosomolytic agent; wherein the particles are on average from about 15 nm to about 300 nm in diameter and wherein the bioactive agent is releasably retained in the particles by the EGCG. In certain embodiments, the endosomolytic agent is polyethylenimine. In certain embodiments, the bioactive agent is releasably retained in the particles by hydrophobic bonds between the EGCG and the bioactive agent. In other embodiments, the bioactive agent is releasably retained in the particles by ionic bonds between the EGCG and the bioactive agent.

Methods of Use

The suspension described herein may be used to deliver a bioactive agent, including an anti-cancer agent, to a cell, including a cancer cell. The HA of the present particles can bind to the CD44 receptor which is overexpressed in many cell types and thus the present particles may specifically target cancer cells for the delivery of the bioactive agent.

Thus in one aspect, there is provided a method for delivery of a bioactive agent to a cell, the method comprising contacting the cell with the suspension or formulation as described herein.

In certain embodiments, the present particle may deliver the bioactive agent directly into the cell. Thus in another aspect, there is presently provided a method for intracellular delivery of a bioactive agent to a cell, the method comprising contacting the cell with the suspension or formulation as described herein.

In particular embodiments, the bioactive agent delivered into the cell may be an agent that ordinarily is unable to traverse the plasma membrane and enter the cell on its own.

In certain embodiments, the cell is a cancer cell. As discussed above, the present particles may selectively target cancer cells for delivery of the bioactive agent.

As used herein, "delivering" a bioactive agent to a cell refers to providing the agent in sufficiently close proximity to the cell such that the agent can exert its biological effects on the cell.

As used herein, "contacting" a cell refers to providing or administering the suspension in a manner that enables the presently described particles to deliver the bioactive agent to the cell. In vitro, for example, contacting the cell may comprise adding the suspension to the cell culture media. In vivo, for example, contacting the cell may comprise administering the suspension to a subject as a pharmaceutical composition.

Following delivery of the bioactive agent to the cell, the bioactive agent may be released from the present particles to exert its biological effects. Without being limited to any particular theory, the bioactive agent may be released from the present particles by disassociation of the particles as a result of the disruption of non-covalent reversible bonds between the bioactive agent and the flavonoid. In different embodiments this disruption may be achieved outside or inside the cell. In particular embodiments, the particle may be disassociated through interaction with molecules of the plasma membrane, interaction with intracellular molecules, through the addition of a disassociation agent, for example Triton-X, or through changes in pH.

In particular embodiments, the bioactive active agent is an anti-cancer agent and the present method provides for delivery of an anti-cancer agent to a cancer cell. In certain embodiments, there is provided delivery of the anti-cancer agent directly into the cell.

In particular embodiments, the cell may be a cell located in a subject in need of treatment for a disease or disorder. For example, the cell may be a cell within a subject having cancer, a subject requiring treatment for cancer or a subject in which prevention of cancer is desired. In some embodiments, the subject is a human subject.

The term "cell" as used herein includes a single cell, a plurality of cells or a population of cells where context permits, unless otherwise specified. The cell may be an in vitro cell, including a cell explanted from a subject. The cell may be a cell grown in batch culture or in tissue culture plates. Alternatively, the cell may be an in vivo cell in a subject. In some embodiments, the subject is a human subject. In certain embodiments, the subject is a subject in need of treatment for a disease or disorder. Similarly, reference to "cells" also includes reference to a single cell where context permits, unless otherwise specified.

As used herein, "cancer cell" refers to any cancer cell that over-expresses the CD44 receptor. A cancer cell refers to a cell that exhibits abnormal cell growth, reduced or loss of control over cell division and the potential to invade nearby tissues. Some cancer cells may display metastasis in which the cell spreads to other locations in the body. Some cancer cells may form tumours. Cancer cells may include, for example, sarcoma, carcinoma, lymphoma or blastoma cells.

"Cancer" as used herein encompasses a class of diseases in which cells exhibit abnormal cell growth and the potential to invade nearby tissues. In some forms of cancer, the abnormal cells may also spread to other locations in the body. Different types of cancer include for example, breast cancer, colorectal cancer, brain cancer, prostate cancer, cervical cancer, ovarian cancer, bone cancer, skin cancer, lung cancer, pancreatic cancer, bladder cancer, gallbladder cancer, kidney cancer, esophageal cancer, Hodgkin lymphoma, non-Hodgkin lymphoma, laryngeal cancer, leukemia, multiple myeloma, oral cancer, pleural mesothelioma, small intestine cancer, testicular cancer, uterine cancer, thyroid cancer and stomach cancer.

The term "treatment" refers to an approach for obtaining beneficial or desired results, including clinical results. Beneficial or desired clinical results can include, but are not limited to, alleviation or amelioration of one or more symptoms or conditions, diminishment of extent of disorder or disease, stabilization of the state of disease, prevention of development of disorder or disease, prevention of spread of disorder or disease, delay or slowing of disorder or disease progression, delay or slowing of disorder or disease onset, amelioration or palliation of the disorder or disease state, and remission, whether partial or total. "Treatment" can also mean prolonging survival of a subject beyond that expected in the absence of treatment. "Treatment" can also mean inhibiting the progression of disorder or disease, slowing the progression of disorder or disease temporarily, although in some instances, it involves halting the progression of the disorder or disease permanently.

The term "effective amount" or "an amount effective" as used herein means an amount effective at dosages and for periods of time necessary to achieve a desired result. For example, the particle may be administered in quantities and dosages necessary to deliver a bioactive agent which may function to alleviate, improve, mitigate, ameliorate, stabilize, prevent the spread of, slow or delay the progression of or cure a disease or disorder, or to inhibit, reduce or impair the activity of a disease-related enzyme. A disease-related enzyme is an enzyme involved in a metabolic or biochemical pathway, which when the pathway is interrupted, or when regulatory control of the enzyme or pathway is interrupted or inhibited, the activity of the enzyme is involved in the onset or progression of a disease or disorder. In particular embodiments, the particle may be administered in quantities and dosages necessary to deliver an anti-cancer agent for the treatment of cancer.

The effective amount of the suspension to be administered to a subject can vary depending on many factors such as the pharmacodynamic properties of the suspension or the particles in the suspension, including the properties of the HA-flavonoid conjugates and the bioactive agent in the particles, the mode of administration, the age, health and weight of the subject, the nature and extent of the disorder or disease state, the frequency of the treatment and the type of concurrent treatment, if any. Furthermore, the effective amount may vary depending on the concentration of the bioactive agent provided in the particles.

One of skill in the art can determine the appropriate amount based on the above factors. The suspension may be administered initially in a suitable amount that may be adjusted as required, depending on the clinical response of the subject. The effective amount of the present suspension can be determined empirically and depends on the maximal amount of the suspension that can be administered safely. However, the amount of suspension administered is preferably the minimal amount that produces the desired result.

Therefore, there is provided a pharmaceutical composition comprising the suspension as described herein. The pharmaceutical composition may further include a pharmaceutically acceptable diluent or carrier. The pharmaceutical composition may routinely contain pharmaceutically acceptable concentration of salts, buffering agents, preservatives and various compatible carriers. For all forms of delivery, the particle may be formulated in a physiological salt solution.

The proportion and identity of the pharmaceutically acceptable diluent or carrier is determined by the chosen route of administration, compatibility with biologically active proteins if appropriate, and standard pharmaceutical practice.

The pharmaceutical composition can be prepared by known methods for the preparation of pharmaceutically acceptable compositions suitable for administration to subjects, such that an effective amount of the particle and any additional active substance or substances is combined in a mixture with a pharmaceutically acceptable vehicle. Suitable vehicles are described, for example, in Remington's Pharmaceutical Sciences (Remington's Pharmaceutical Sciences, Mack Publishing Company, Easton, Pa., USA 1985). On this basis, the compositions may include the particle in association with one or more pharmaceutically acceptable vehicles or diluents, and contained in buffer solutions with a suitable pH and iso-osmotic with physiological fluids.

Under ordinary conditions of storage and use, such pharmaceutical compositions may contain a preservative to prevent the growth of microorganisms, and that will maintain any biological activity of the particle and the bioactive agent. A person skilled in the art would know how to prepare suitable formulations. Conventional procedures and ingredients for the selection and preparation of suitable formulations are described, for example, in Remington's Pharmaceutical Sciences and in The United States Pharmacopeia: The National Formulary (USP 24 NF19) published in 1999. Alternatively, the flavonoid conjugate hydrogel may be formulated at a time sufficiently close to use by mixing the components, without the need for preservatives.

Thus in one aspect, there is provided, a therapeutic formulation comprising the suspension as described herein. In another aspect, there is provided a method of treating a disease comprising administering to a subject in need thereof an effective amount of the suspension or formulation as described herein.

Uses of the suspension and formulation describe herein for delivery of a bioactive agent to a cell and in the preparation of a medicament for delivery of a bioactive agent to a cell are also contemplated.

Uses of the suspension and formulation describe herein for intracellular delivery of a bioactive agent to a cell and in the preparation of a medicament for intracellular delivery of a bioactive agent to a cell are also contemplated.

The present methods and compounds are further exemplified by way of the following non-limiting examples.

EXAMPLES

Materials.

Sodium hyaluronate (HA) (MW=90 KDa, density=1.05 g/cm$^3$) was kindly provided by Chisso Corporation (Tokyo, Japan). Diethoxyethyl amine (DA), N-hydroxysuccinimide (NHS), 1-ethyl-3-(3-dimethylaminopropyl)-carbodiimide hydrochloride (EDC-HCl), lysozyme from chicken egg white and *Micrococcus lysodeikticus* were all purchased from Sigma-Aldrich. Lissamine rhodamine B ethyldiamine and fluorescein isothiocynate (FITC) were purchased from Invitrogen. Phosphate buffer saline (PBS, 150 mM, pH 7.3) was supplied by media preparation facility in Biopolis, Singapore.

ExGen 500 Transfection Reagent (Linear poly(ethyleneimine) (PEI) 22 kDa) was purchased from Fermentas INC. Mouse Granzyme B and chloroquine diphosphate were purchased from Sigma-Aldrich. Alamarblue (100 ml) was purchased from Invitrogen.

Synthesis of HA-DA Conjugates.

HA (5 g, 12.5 mmol) was dissolved in 500 ml of distilled water. To this diethoxyethyl amine (DA) with different amounts (1.19 g, 8.93 mmol) or (2.38 g, 17.8 mmol) was added followed by NHS (1.16 g, 10.0 mmol) and EDC (2.40 g, 12.5 mmol) to initiate the conjugation reaction. As the reaction proceeded, the pH of the mixture was maintained at 4.7 by the addition of 0.1 M NaOH. The reaction mixture was stirred overnight at room temperature and then the pH was adjusted to 7.0. The solution was transferred to dialysis tubes with molecular cut-off of 1000 Da. The tubes were dialyzed against 100 mM sodium chloride solution for 2 days, a mixture of distilled water and ethanol (3:1) for 1 day and distilled water for 1 day, successively. The purified solution was lyophilized to obtain the HA-DA. The degree of substitution (the number of DA molecules per 100 repeating units of HA) was calculated from $^1$H NMR measurement by comparing the ratio of the relative peak integrations of methyl protons of DA and the methyl protons of HA. The degree of substitution was 16.8%.

Synthesis of HA-EGCG Conjugates.

HA-DA conjugates (1 g) were dissolved in 57 ml of distilled water. The solution was then degassed by bubbling nitrogen through the solution for 20 min. EGCG solution was dissolved in 13 ml of degassed DMSO. The EGCG solution (20 equivalents of molar concentration with respect to the DA units) was then added to the solution of HA-DA conjugate. The pH of the solution was adjusted to 1.0 using concentrated HCl. The resulting solution was then stirred at room temperature for 24 h under a nitrogen atmosphere. The solution was transferred to dialysis tubes with a molecular cut-off of 3500 Da and dialyzed against water under a nitrogen atmosphere for 3 days. The purified solution was lyophilized to obtain the HA-EGCG conjugate. The degree of substitution (the number of bis-EGCG molecules per 100 repeating units of HA) was calculated by the UV-VIS measurements.

Synthesis of HA-EGCG-Rhodamine (HAER).

100 mg of HA-EGCG was dissolved in 10 ml of distilled water that had been continuously degassed with nitrogen for 15 min. 1 mg of Lissamine rhodamine B ethyldiamine (Invitrogen) was dissolved in 1 ml of DMSO, protected from light, and degassed with nitrogen for 15 min. The rhodamine B solution was then added to HA-EGCG solution and the pH was adjusted rapidly to 4.5 to facilitate the Schiff base formation between the primary amine on Lissamine rhodamine B ethyldiamine and the free aldehyde groups on the main chain of HA-EGCG. Meanwhile, continuous purging of the reaction mixture with nitrogen was carried out. The pH was maintained for 3 h, after which the reaction mixture was dialyzed against 100 mM sodium chloride solution for 2 days, a mixture of distilled water and ethanol (3:1) for 1 day and distilled water for 1 day, successively and always under a nitrogen atmosphere. The fluorescence of the final dialysate was measured to determine whether free rhodamine dye (EX: 560-575 nm, EM: 580-595 nm) was still present. If so, dialysis was carried out for one more day in distilled water. The purified solution was lyophilized to obtain the HA-EGCG-rhodamine.

Synthesis of FITC-Lysozyme (FL).

300 mg of lysozyme was dissolved in 60 ml of 0.1 M borate buffer (pH 8.5). 12 mg of FITC was dissolved in another 60 ml of borate buffer. The FITC solution was added drop-wise to the lysozyme solution while stirring in the dark. The solution was left stirring gently for 16 h, after which it was dialyzed against distilled water at 4° C. for 3 days, refreshing the distilled water twice daily. The resultant solution was lyophilized.

Preparation of HA-EGCG/Lysozyme Particles.

HA-EGCG was dissolved in distilled water at a stock concentration of 10 mg/ml by vortexing for 5 min and sonication for 10 min. This HA-EGCG stock solution was subsequently diluted in PBS to the respective working concentrations. Lysozyme was dissolved in PBS. Particles were synthesized at room temperature by simply mixing the HA-EGCG and lysozyme solutions with gentle pipetting, and then leaving the mixtures to sit for 10 min. The composition of the particles was varied by changing the working concentrations of either HA-EGCG or lysozyme.

Dynamic Light Scattering (DLS).

The size of HA-EGCG/lysozyme particle was evaluated by DLS using a particle sizer (Brookhaven instruments Co.) The DLS measurement was carried out at a concentration of 0.75, 1 or 2 mg/ml samples at 25° C.

Fluorescence Quenching Studies.

The fluorescence emission spectra of the HA-EGCG/lysozyme particles, HA/lysozyme mixtures, free lysozyme alone, free HA-EGCG carrier or free HA alone were measured at an excitation wavelength of 280 nm using a fluorescence spectrophotometer (Hitachi, Japan). Difference spectra between the HA-EGCG/lysozyme particles and HA-EGCG were obtained to determine the net fluorescence of lysozyme in particles of varying HA-EGCG concentrations. The same was done for HA/lysozyme mixtures.

Lysozyme Activity Assay.

To determine the activity of lysozyme, 20 µl of sample containing either free lysozyme or HA-EGCG/lysozyme particles was added to a well of a 96-well assay plate, followed by 100 µl of *M. lysodeikticus* (0.15% (w/v) in PBS). The decrease in turbidity was monitored by a Tecan Infinite 200 microplate reader by measuring the absorbance of the sample at 450 nm at room temperature every 3 min for 15 min. The absorbance decay plot was fitted to a linear equation, and the slopes were used to determine lysozyme activity. Regarding the restoration of activity of lysozyme that is complexed with HA-EGCG, the following protocol was used: the HA-EGCG/lysozyme particles were first allowed to self-assemble for 10 min at room temperature, with free lysozyme diluted with PBS as a control. A constant volume of Triton-X of different concentrations was then added to each sample (to a final concentration of 0.001, 0.01 or 0.1% w/v), incubated at room temperature for a further 5 min before the lysozyme substrate, *M. lysodeikticus*, was added, and the absorbance monitored as described above.

Circular Dichroism (CD) Spectroscopy.

Far-ultraviolet CD spectra were obtained using an Olis spectropolarimeter. A cylindrical quartz cuvette with 0.5 mm path length was used. The ellipticity was measured every 1 nm with an integration time of 1 s. Three sequential spectra were recorded and averaged for each sample. The difference spectrum between the HA-EGCG/lysozyme particles and HA-EGCG carrier was obtained and compared with the spectrum of lysozyme alone. The results are expressed in terms of millidegrees.

Cell Culture.

HCT-116 human colon carcinoma cells were obtained from ATCC, and cultured in McCoy's 5A medium supplemented with 10% FBS and 100 units/mL of penicillin/streptomycin.

Cellular Uptake Studies.

HCT-116 cells were seeded at 20,000 cells per well in 8-well LabTek chambered glass slides with complete growth medium and left to attach for 48 h. The medium was aspirated and the cells were gently washed with serum-free medium once before FL, HAER, HAR, HAER/FL, HAR/FL (all diluted in serum-free medium) were added and the cells were incubated at growth conditions for 4 h respectively. The solutions were then removed, and the cells were washed twice with PBS, fixed with 4% formaldehyde at room temperature for 15 min, washed twice with PBS, stained with 1 µg/ml of Hoechst 33358 to elucidate the nuclei, and finally washed twice with PBS. Confocal images were obtained with a Carl Zeiss LSM 5 DUO inverted confocal microscope with a 63× objective and 488 nm, 543 nm lasers for excitation of FITC and rhodamine B respectively. The confocal images were quantified with Metamorph program. The background fluorescence intensity of 25 random spots was measured, averaged, and subtracted from the average FITC or rhodamine B fluorescence intensity of 25 random spots that represented the extent of lysozyme and HAER/HAR uptake, respectively.

Cell Viability Studies:

HCT-116 cells were seeded at 10,000 cells per well in 96-well microplates with complete growth medium and left to attach for 48 h. Test reagents were prepared by first mixing the linear PEI (polyethylenimine) or chloroquine solution (fixed at 100 µM)) with Granzyme B (fixed at 2 µg/ml) for 15 min before adding HA-EGCG solution to the mixture and allow complexation to take place for 45 min. The medium in the wells was then aspirated and the cells were treated with the respective reagents for 48 h (all dilutions were made in serum-free medium). Cell viability was analyzed using AlamarBlue. Before analysis, the medium was aspirated and the cells were gently washed with PBS once before a mixture of 10 µl of alamarblue reagent with 100 µl of serum-containing medium was added to each well. The cells were incubated for 2 h and the fluorescence emission of each well was measured using a Tecan Infinite Microplate Reader. The viabilities of treated cells were evaluated as a percentage of the negative control. Each data set is an average of 4 repeats.

Results

Figure 2:
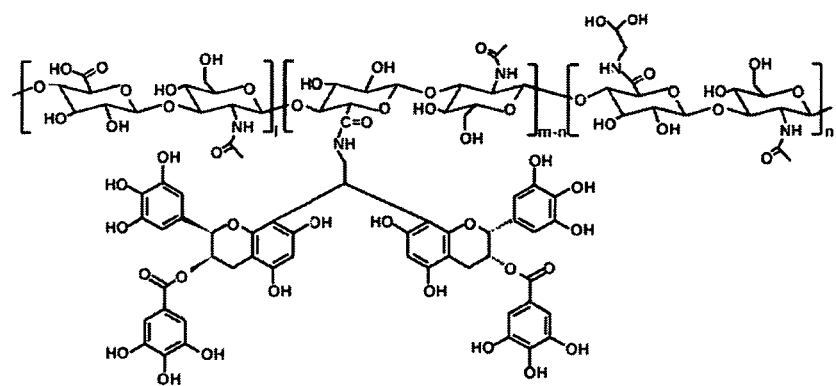
FIG. 2. Chemical structure of HA-EGCG conjugates.

HA-EGCG was synthesized by a two-step reaction procedure, as previously described. HA-diethoxyethylamine (HA-DA) conjugate was first prepared by a standard carbodiimide/active ester mediated-coupling reaction. This was followed by the conjugation of EGCG to HA via a Baeyer acid-catalyzed reaction between a nucleophilic A ring of EGCG and an aldehyde group which was formed by the deprotection of the diethoxy acetal group of HA-DA under acidic conditions (FIG. 2).

Figure 3:
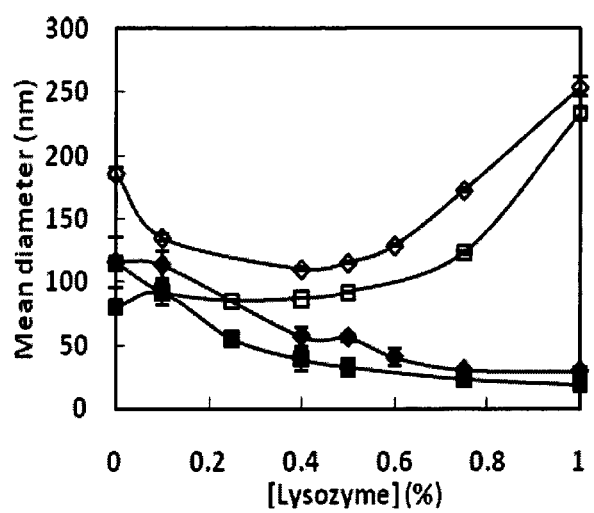
FIG. 3. Effect of lysozyme concentration on particle size of HA-EGCG/lysozyme particles (□: HA-EGCG 0.75 mg/ml, ■: HA 0.75 mg/ml, ◊: HA-EGCG 1 mg/ml, ♦: HA 1 mg/ml).

The complexation behavior between HA-EGCG and a model protein, lysozyme, was first studied by dynamic light scattering. Particles of HA-EGCG and lysozyme that were on the order of 100 nm could be prepared. HA-EGCG/lysozyme particles prepared with a fixed concentration of HA-EGCG and varying lysozyme concentrations showed a biphasic behavior, with an initial decrease in particle size and a subsequent increase in particle size with increasing lysozyme concentration (FIG. 3). As a control, a fixed concentration of unmodified HA was mixed with lysozyme of different concentrations, and it was observed that there was a monotonic decrease in particle size with increasing lysozyme concentrations. This difference may be attributed to the hydrophobic EGCG moiety, which may allow the HA-EGCG particles to be formed via both ionic and hydrophobic interactions. In fact, at very high lysozyme concentrations (>0.75% w/v), HA-EGCG/lysozyme particles become increasingly turbid and start to phase separate from solution when left to stand due to extensive hydrophobic interactions. In contrast, HA/lysozyme mixtures do not phase separate at the same protein concentrations.

Figure 4:
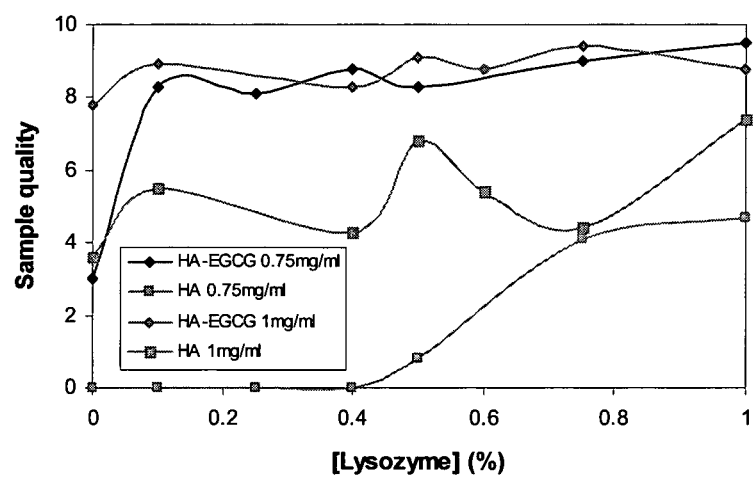
FIG. 4. Effect of lysozyme concentration on particle homogeneity (measured as sample quality) of HA-EGCG/lysozyme suspension.

The sample quality of HA-EGCG/lysozyme particles was also consistently higher than that of HA/lysozyme mixtures (FIG. 4). Sample quality refers to the difference between the measured baseline and calculated baseline of the autocorrelation function, and in practical terms, a low sample quality indicates the presence of large particles or aggregates. Hence, HA-EGCG/lysozyme particles are more stable and homogeneous than HA/lysozyme mixtures.

Figure 5:
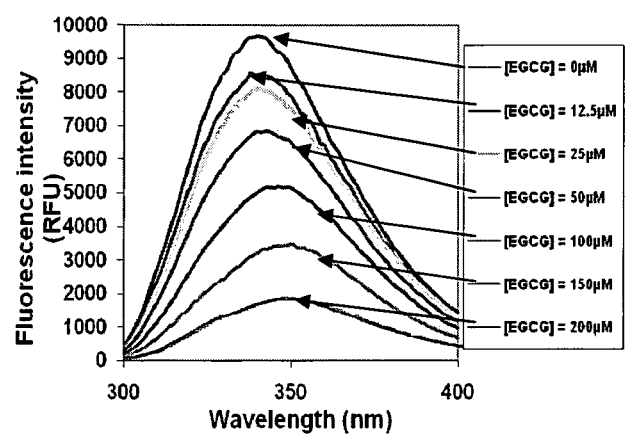
FIG. 5. EGCG quenches the intrinsic fluorescence of lysozyme (EX: 280 nm) in a concentration-dependent manner.
Figure 6:
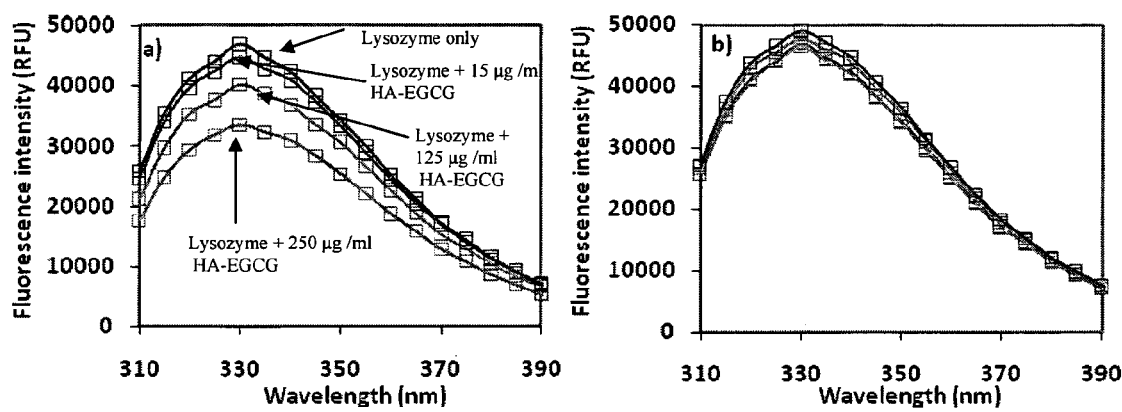
FIG. 6. EGCG moiety is important for the binding interaction between HA-EGCG and lysozyme. HA-EGCG (a) quenches intrinsic lysozyme fluorescence in a concentration-dependent manner, and to a larger extent than HA (b). [lysozyme]=250 μg/ml. Blue: Lysozyme only, Brown: Lysozyme+15 μg/ml HA or HA-EGCG, Green: Lysozyme+125 μg/ml HA or HA-EGCG, Red: Lysozyme+250 μg/ml HA or HA-EGCG.
Figure 7:
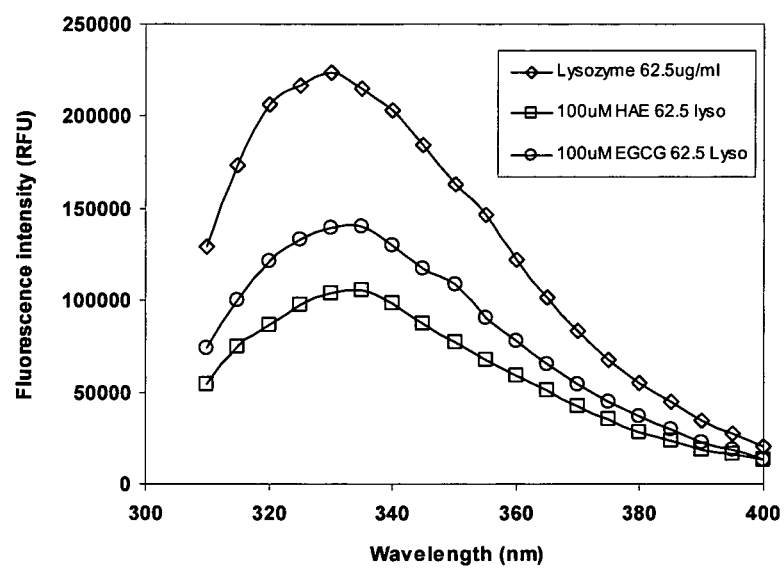
FIG. 7. Conjugation of EGCG to HA increases the extent to which the intrinsic fluorescence of lysozyme is quenched at a constant EGCG concentration.

To confirm that the EGCG moiety is indeed necessary for HA-EGCG to efficiently bind protein, use was made of the fact that EGCG can quench the intrinsic fluorescence of lysozyme[13] in a concentration-dependent manner (FIG. 5). It was observed that HA-EGCG significantly decreases intrinsic lysozyme fluorescence compared with HA (FIGS. 6a & 6b). Furthermore, it was noted that free EGCG quenches intrinsic lysozyme fluorescence to a smaller degree than HA-EGCG with the same EGCG concentration (FIG. 7), which shows that the conjugation of EGCG to HA enhances the binding interaction between EGCG and lysozyme, possibly because the HA backbone increases the local concentration of EGCG moieties around a lysozyme molecule.

Figure 8:
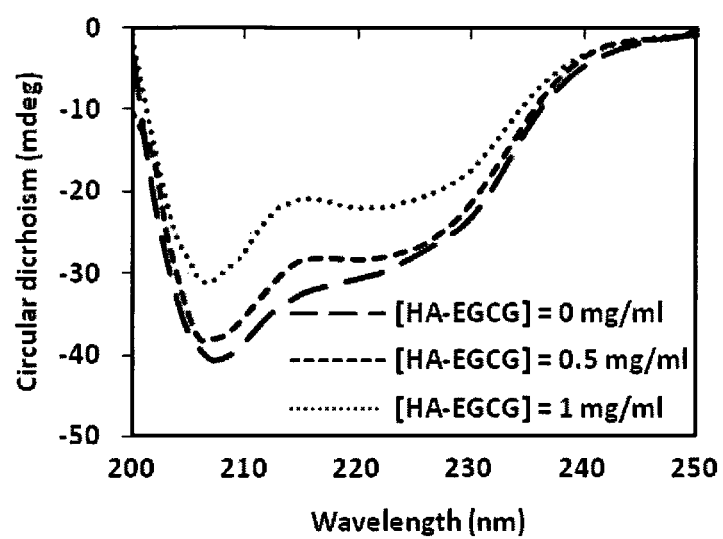
FIG. 8. HA-EGCG decreases the secondary structure content of lysozyme. [lysozyme]=0.5 mg/ml.

Deducing that the quenching of intrinsic lysozyme fluorescence by HA-EGCG could correlate to a partial denaturation of lysozyme, the secondary structure of lysozyme was studied in its free form and in HA-EGCG/lysozyme particles by circular dichroism spectroscopy. The difference spectrum of HA-EGCG/lysozyme and HA-EGCG alone was obtained to extract information about the lysozyme secondary structure. The ellipticity at 220 nm is a standard measure of helical content of a protein and was used to estimate the secondary structural change of the protein. As HA-EGCG concentration increases, the ellipticity at 220 nm decreased (FIG. 8), indicating a partial denaturation of lysozyme.

Figure 9:
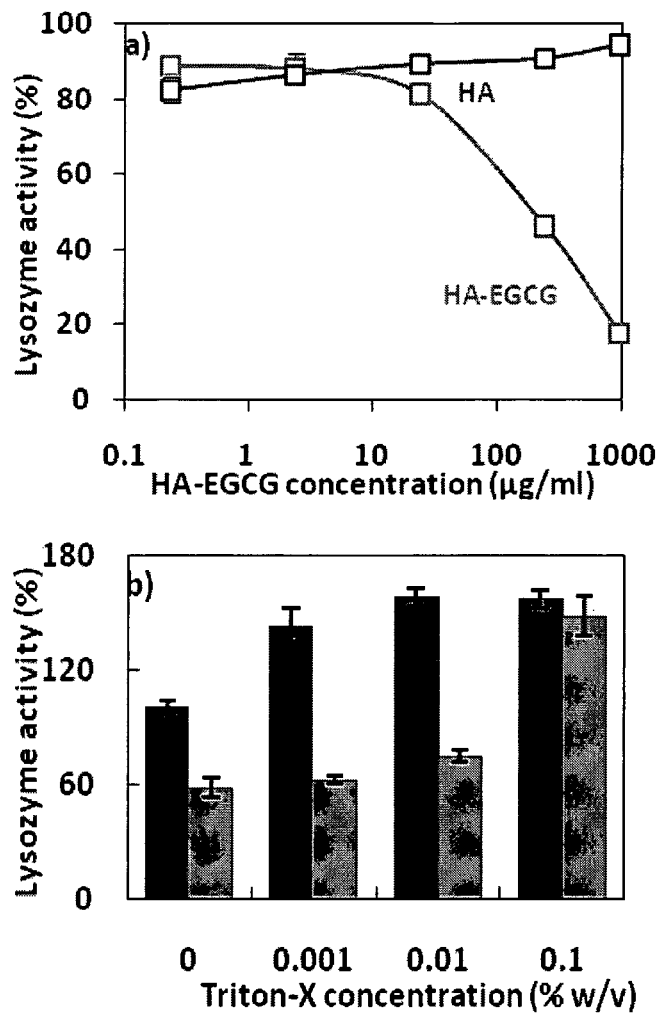
FIG. 9. Lysozyme activity. a) Inhibition of lysozyme activity at higher concentrations of HA-EGCG. [lysozyme]=10 μg/ml. Red: HA-EGCG, blue: HA. b) Adding Triton-X to HA-EGCG/lysozyme particles restores lysozyme activity that is lost during complexation with HA-EGCG. Blue bar (left bars): lysozyme only, red bars (right bars): HA-EGCG/lysozyme particle.

The complexation of HA-EGCG with lysozyme can also be shown by an inhibition in lysozyme activity with an increase in HA-EGCG concentration. Using *M. lysodeikticus* as the lysozyme substrate[14], it was found that HA-EGCG decreased lysozyme activity in a concentration-dependent manner, whereas HA does not (FIG. 9a).

As delivery of a functional protein into the cell was sought, efficient complexation was not sufficient. Dissociation of the complex to release the functional protein was also desired once the particle is internalized within the cell, so that the protein can achieve its intended function. In order to demonstrate that this is possible, the pre-formed HA-EGCG/lysozyme particles were destablized with Triton-X, which is expected to disrupt the hydrophobic interactions[15] within the complex. For the free lysozyme control, it was noted that merely adding a low concentration of Triton-X (0.001% w/v) increases its apparent activity to 140% of its original activity (FIG. 9b). This is reasonable, considering that some free lysozyme can adhere to the hydrophobic plastic well and become partially denatured in the absence of Triton-X. Further increasing Triton-X concentrations by two orders of magnitude (0.01% and 0.1%) result in a plateau in the apparent lysozyme activity, which reaches its maximum activity at about 160%. For the HA-EGCG/lysozyme (comprising 50 µM HA-EGCG and 20 µg/ml lysozyme) complexes, adding 0.001% or 0.01% Triton-X did not significantly restore lysozyme activity, which remained close to 60% (FIG. 9b). However, when 0.1% Triton-X was added, sufficient disruption of hydrophobic interactions within the HA-EGCG/lysozyme particles occurred, resulting in an almost complete restoration of lysozyme activity to its maximum level under these experimental conditions.

Figure 10:
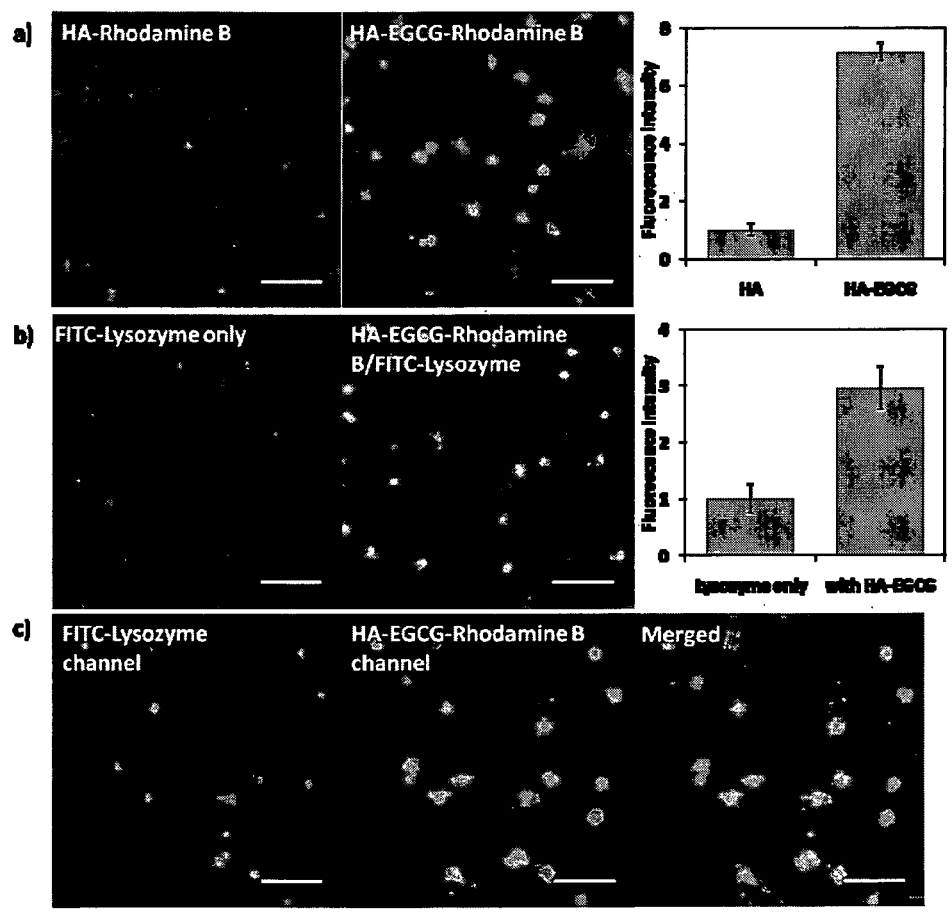
FIG. 10. Cellular internalization of HA-EGCG a) Rhodamine B-labeled HA-EGCG is internalized by HCT-116 cells much more efficiently than Rhodamine B-labeled HA. b) Lysozyme is internalized more efficiently by HCT-116 cells when delivered with HA-EGCG as a carrier than without HA-EGCG. c) Colocalization of HA-EGCG-rhodamine B and FITC-lysozyme shows that the increased lysozyme uptake is due to HA-EGCG acting as a carrier for lysozyme.

It was found that rhodamine B-labelled HA-EGCG (HAER) could be internalized by HCT-116 human colon carcinoma cells more efficiently than rhodamine B-labelled HA (HAR) (FIG. 10a). Furthermore, particles of unlabelled HA-EGCG and FITC-labelled lysozyme (HAE/FL) were found to more efficiently deliver lysozyme into HCT-116 cells than either mixtures of HA and FITC-labelled lysozyme (HA/FL) or without a delivery system (free protein, FL, itself) (FIG. 10b). This is reasonable, since HA/lysozyme mixtures do not form very good complexes, and free lysozyme is like taken up by pinocytosis, which is much less efficient that receptor-mediated endocytosis. The colocalization of rhodamine B and FITC in cells treated with HAER/FL particles further confirms that the increased uptake of lysozyme is indeed due to HA-EGCG acting as a carrier for lysozyme (FIG. 10c).

Figure 11:
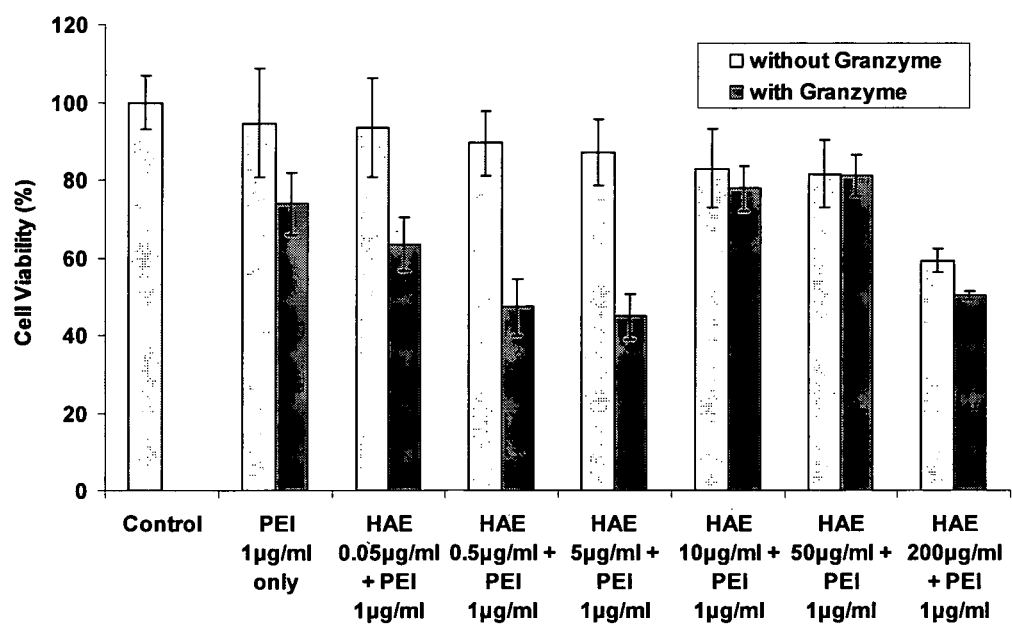
FIG. 11. Cell viability of HCT-116 cells incubated with particles comprising HA-EGCG, Granzyme and PEI.

In order to further develop the concept of intracellular delivery of a functional protein using the present HA-EGCG particles, Granzyme B was used. Granzyme B is a protease normally secreted by the Cytotoxic T Lymphocytes (CTLs) of the immune system to kill virus-infected cells. It does so through the activation of caspase intracellularly which triggers a cascade of reactions that induce apoptosis. Granzyme, when delivered together with chloroquine, induced cytotoxicity in HCT-116 cells (data not shown). Chloroquine is an endosomolytic agent that can facilitate the escape of cargoes from endosomes. It is necessary to combine chloroquine with Granzyme B when treating the cells to allow Granzyme B to be released into the cytosol where it can activate its target. Also, particles comprising HA-EGCG and Granzyme in the presence of chloroquine showed apoptosis of the cell. However, the particles containing chloroquine are not appropriate due to the toxicity of chloroquine. Therefore, particles were designed comprising HA-EGCG, Granzyme and PEI for intracellular delivery of protein drugs. It is well known that PEI is an endosomolytic agent and destabilizes endosomes in cells. It was observed that the cell viability decreased by using particles containing PEI (FIG. 11). 5 µg/ml of HA-EGCG showed the most significant Granzyme effect. Also, the effect of Granzyme decreased when higher concentration of HA-EGCG was utilized. These results indicate that the combination of the processes of destabilization of HA-EGCG and Granzyme complex and escape of Granzyme from endosomes is possibly most efficient when 5 µg/ml HA-EGCG was utilized. From the results, it was concluded that the HA-EGCG particles have achieved successful delivery of a functional intrabody, Granzyme B, into the cytosol of HCT-116 cells.

Although various embodiments of the invention are disclosed herein, many adaptations and modifications may be made within the scope of the invention in accordance with the common general knowledge of those skilled in this art. Such modifications include the substitution of known equivalents for any aspect of the invention in order to achieve the same result in substantially the same way.

Numeric ranges are inclusive of the numbers defining the range.

All technical and scientific terms used herein have the same meaning as commonly understood by one of ordinary skill in the art of this invention, unless defined otherwise.

Concentrations given in this specification, when given in terms of percentages, include weight/weight (w/w), weight/volume (w/v) and volume/volume (v/v) percentages.

The word "comprising" is used herein as an open-ended term, substantially equivalent to the phrase "including, but not limited to", and the word "comprises" has a corresponding meaning. As used herein, the singular forms "a", "an" and "the" include plural referents unless the context clearly dictates otherwise. Thus, for example, reference to "a thing" includes more than one such thing.

Citation of references herein is not an admission that such references are prior art to the present invention. Any priority document(s) and all publications, including but not limited to patents and patent applications, cited in this specification are incorporated herein by reference as if each individual publication were specifically and individually indicated to be incorporated by reference herein and as though fully set forth herein.

The invention includes all embodiments and variations substantially as hereinbefore described and with reference to the examples and drawings. In some embodiments, the invention excludes steps that involve medical or surgical treatment.

REFERENCES

1. Park, J. W.; Kirpotin, D. B.; Hong, K.; Shalaby, R.; Shao, Y.; Nielsen, U. B.; Marks, J. D.; Papahadjopoulos, D.; Benz, C. C., Tumor targeting using anti-her2 immunoliposomes. *J Control Release* 2001, 74, (1-3), 95-113.
2. Senter, P. D.; Springer, C. J., Selective activation of anti-cancer prodrugs by monoclonal antibody-enzyme conjugates. *Adv Drug Deliv Rev* 2001, 53, (3), 247-64.
3. Wheeler, Y. Y.; Chen, S. Y.; Sane, D. C., Intrabody and intrakine strategies for molecular therapy. *Mol Ther* 2003, 8, (3), 355-66.
4. Kontermann, R. E., Intrabodies as therapeutic agents. *Methods* 2004, 34, (2), 163-70.
5. Tse, E.; Rabbitts, T. H., Intracellular antibody-caspase-mediated cell killing: an approach for application in cancer therapy. *Proc Natl Acad Sci USA* 2000, 97, (22), 12266-71.
6. Heng, B. C.; Cao, T., Making cell-permeable antibodies (Transbody) through fusion of protein transduction domains (PTD) with single chain variable fragment (scFv) antibodies: potential advantages over antibodies expressed within the intracellular environment (Intrabody). *Med Hypotheses* 2005, 64, (6), 1105-8.
7. Bourguignon, L. Y.; Zhu, H.; Shao, L.; Chen, Y. W., CD44 interaction with tiam1 promotes Rac1 signaling and hyaluronic acid-mediated breast tumor cell migration. *J Biol Chem* 2000, 275, (3), 1829-38.
8. Matsubara, Y.; Katoh, S.; Taniguchii, H.; Oka, M.; Kadota, J.; Kohno, S., Expression of CD44 variants in lung cancer and its relationship to hyaluronan binding. *J Int Med Res* 2000, 28, (2), 78-90.
9. Shimizu, T.; Kishida, T.; Hasegawa, U.; Ueda, Y.; Imanishi, J.; Yamagishi, H.; Akiyoshi, K.; Otsuji, E.; Mazda, 0., Nanogel DDS enables sustained release of IL-12 for tumor immunotherapy. *Biochem Biophys Res Commun* 2008, 367, (2), 330-5.

10. Kirker, K. R.; Luo, Y.; Nielson, J. H.; Shelby, J.; Prestwich, G. D., Glycosaminoglycan hydrogel films as bio-interactive dressings for wound healing. *Biomaterials* 2002, 23, (17), 3661-71.
11. Maiti, T. K.; Ghosh, K. S.; Dasgupta, S., Interaction of (−)-epigallocatechin-3-gallate with human serum albumin: fluorescence, fourier transform infrared, circular dichroism, and docking studies. Proteins 2006, 64, (2), 355-62.
12. Abe, I.; Kashiwagi, K.; Noguchi, H., Antioxidative galloyl esters as enzyme inhibitors of p-hydroxybenzoate hydroxylase. *FEBS Lett* 2000, 483, (2-3), 131-4.
13. Rawel, H. M.; Frey, S. K.; Meidtner, K.; Kroll, J.; Schweigert, F. J., Determining the binding affinities of phenolic compounds to proteins by quenching of the intrinsic tryptophan fluorescence. *Mol Nutr Food Res* 2006, 50, (8), 705-13.
14. Kurschus, F. C.; Kleinschmidt, M.; Fellows, E.; Dornmair, K.; Rudolph, R.; Lilie, H.; Jenne, D. E., Killing of target cells by redirected granzyme B in the absence of perforin. FEBS Lett 2004, 562, (1-3), 87-92.
15. Zordan-Nudo, T.; Ling, V.; Liu, Z.; Georges, E., Effects of nonionic detergents on P-glycoprotein drug binding and reversal of multidrug resistance. *Cancer Res* 1993, 53, (24), 5994-6000.
16. Jankun J., et al. *Nature* 387, 561 (1997).
17. Bodoni A. et al. *J. Nutr. Biochem.* 13, 103-111 (2002).
18. Nakagawa K. et al. *J. Agric. Food Chem.* 47, 3967-3973 (1999).
19. Terao J., et al. *Arch. Biochem. Biophys.* 308, 278-284 (1994).
20. Isemura M., et al. *Biofactors* 13, 81-85 (2000).
21. Ikeda I., et al. *J. Nutr.* 135, 155 (2005).
22. Lill G., et al. *FEBS Letters* 546, 265-270 (2003).
23. Sakanaka S. and Okada Y. *J. Agric. Food Chem.* 52, 1688-1692 (2004).
24. Yokozawa T., et al., *J. Agric. Food Chem.* 48, 5068-5073 (2000).
25. Jankun, J., Selman, S. H., Swiercz, R., Why drinking green tea could prevent cancer, Nature, 387, 561 (1997).
26. Garbisa, S., Biggin, S., Cavallarin, N., Sartor, L., Benelli, R., Albini, A., Tumor invasion: molecular shears blunted by green tea, Nature medicine, 5(11), 1216 (1999).
27. Tachibana, H., Koga, K., Fujimura, Y., Yamada, K., A receptor for green tea polyphenol EGCG, Nature Structural & Molecular Biology, 11(4), 380-381 (2004).
28. Nagle, D. G., Ferreira, D., Zhou, Y. D., Epigallocatechin-3-gallate (EGCG): chemical and biomedical perspectives, Phytochemistry, 67, 1849-1855 (2006).
29. Sang, S., Yang, I., Buckley, B., Ho, C. T., Yang, C. S., Autooxidative quinine formation in vitro and metabolite formation in vivo from tea polyphenol (−)-epigallocatechin-3-gallate: studied by real-time mass spectrometry combined with tandem mass ion mapping, Free Radical Biology & Medicine, 43, 362-371 (2007).
30. Yang, C. S., Wang, Z. Y., Tea and cancer, Journal of the National Cancer Institute, 85(13), 1038-1049 (1993).
31. Garbisa, S., Sartor, L., Biggin, S., Salvato, B., Benelli, R., Albini, A., Tumor gelatinases and invasion inhibited by the green tea flavanol epigallocatecin-3-gallate, Cancer, 91(4), 822-832, (2001).

What is claimed is:

1. A suspension of immiscible particles in an aqueous solution, the particles comprising an agglomeration of:
   a bioactive agent; and
   a plurality of conjugates of a hyaluronic acid and a flavonoid;
   the particles having a hydrated interior and having an average diameter of from about 15 nm to about 300 nm, the bioactive agent being releasably retained in the particles by the flavonoid.
2. The suspension of claim 1 wherein the bioactive agent is releasably retained in the particles by a hydrophobic bond or an ionic bond between the flavonoid and the bioactive agent.
3. The suspension of claim 1 wherein the particles are on average from about 50 nm to about 100 nm in diameter.
4. The suspension of claim 1 wherein the flavonoid is a catechin-based flavonoid.
5. The suspension of claim 4 wherein the flavonoid is epigallocatechin gallate.
6. The suspension of claim 1 wherein the bioactive agent is an anti-cancer agent.
7. The suspension of claim 1 wherein the bioactive agent is a protein.
8. The suspension of claim 1 wherein the bioactive agent is an intrabody.
9. The suspension of claim 1 wherein the bioactive agent is Granzyme B.
10. The suspension of claim 1, wherein the HA has a molecular weight of from about 5000 to about 10000000 daltons.
11. The suspension of claim 1 wherein the particles further comprise an endosomolytic agent.

* * * * *